(12) United States Patent
Harada-Shiba et al.

(10) Patent No.: US 11,273,222 B2
(45) Date of Patent: Mar. 15, 2022

(54) ANTISENSE NUCLEIC ACID TARGETING PCSK9

(71) Applicant: National Cerebral and Cardiovascular Center, Osaka (JP)

(72) Inventors: Mariko Harada-Shiba, Osaka (JP); Fumito Wada, Osaka (JP); Satoshi Obika, Osaka (JP); Tsuyoshi Yamamoto, Osaka (JP); Keisuke Tachibana, Osaka (JP); Tadayuki Kobayashi, Osaka (JP); Kosuke Ito, Osaka (JP); Motoki Sawamura, Osaka (JP)

(73) Assignee: National Cerebral and Cardiovascular Center, Osaka (JP)

( * ) Notice: Subject to any disclaimer, the term of this patent is extended or adjusted under 35 U.S.C. 154(b) by 158 days.

(21) Appl. No.: 16/616,724

(22) PCT Filed: May 24, 2018

(86) PCT No.: PCT/JP2018/020081
§ 371 (c)(1),
(2) Date: Nov. 25, 2019

(87) PCT Pub. No.: WO2018/216785
PCT Pub. Date: Nov. 29, 2018

(65) Prior Publication Data
US 2021/0170032 A1 Jun. 10, 2021

(30) Foreign Application Priority Data

May 26, 2017 (JP) .............................. JP2017-105121

(51) Int. Cl.
*A61K 47/54* (2017.01)
*A61P 3/06* (2006.01)
*C12N 15/113* (2010.01)

(52) U.S. Cl.
CPC .............. *A61K 47/549* (2017.08); *A61P 3/06* (2018.01); *C12N 15/1137* (2013.01); *C12N 2310/11* (2013.01); *C12N 2310/315* (2013.01); *C12N 2310/3231* (2013.01); *C12N 2310/351* (2013.01)

(58) Field of Classification Search
None
See application file for complete search history.

(56) References Cited

U.S. PATENT DOCUMENTS

| | | |
|---|---|---|
| 2009/0292006 A1 | 11/2009 | Bhanot et al. |
| 2010/0216864 A1 | 8/2010 | Straarup et al. |
| 2012/0122954 A1 | 5/2012 | Straarup et al. |
| 2015/0291958 A1 | 10/2015 | Albaek et al. |
| 2015/0368642 A1 | 12/2015 | Albaek et al. |
| 2016/0138025 A1 | 5/2016 | Albaek et al. |
| 2017/0355727 A1 | 12/2017 | Seth et al. |
| 2018/0311365 A1* | 11/2018 | Swayze ................ A61K 47/549 |

FOREIGN PATENT DOCUMENTS

| | | |
|---|---|---|
| JP | 2009-536037 A | 10/2009 |
| JP | 2010-505432 A | 2/2010 |
| JP | 2016-508367 A | 3/2016 |
| JP | 2016-523094 A | 8/2016 |
| WO | WO 2015/179693 A1 | 11/2014 |
| WO | WO 2014/207232 A1 | 12/2014 |

OTHER PUBLICATIONS

Cohen, Jonathan C. et al., "Sequence Variations in PCSK9, Low LDL, and Protection against Coronary Heart Disease" N Engl J Med, 2006, pp. 1264-1272, vol. 354.
Shiba, Mariko "Antisense Drug Discovery and Development for Familial Hypercholesterolemia" Abstract of the 17$^{th}$ symposium of Research Society of Gene Delivery, May 27, 2017, p. 13.
Shiba, Mariko "Development of antisense drug targeting familial hypercholesterolemia", Lecture abstract of the 3$^{rd}$ annual conference of Nucleic Acids Therapeutics Society of Japan, Jul. 1, 2017, p. 42; S4-2.
Wada, Fumito et al., "Efficient Screening of Antisense Oligonucleotides Targeting PCSK9 and Evaluating the Drug Effectiveness in Nonhuman Primates", Lecture abstracts of the 2$^{nd}$ annual conference of Nucleic Acids Therapeutics Society of Japan, 2016, p. 102; p. 44.
Wada, Fumito et al., "Optimization of anti-PCSK9 antisense oligonucleotides and the pre-clinical studies using rodents and nonhuman primates", Abstract of the 17$^{th}$ symposium of Research Society of Gene Delivery, May 27, 2017, p. 32; p. 16.
Wada, Fumito et al., "Evaluating safety and efficacy of GalNAc-conjugated anti-PCSK9 antisense using rodents and non-human primates", Lecture abstract of the 3$^{rd}$ annual conference of Nucleic Acids Therapeutics Society of Japan, Jul. 1, 2017, p. 33; 02-2.
Yamamoto, Tsuyoshi et al., "Serial incorporation of a monovalent GalNAc phosphoramidite unit into hepatocyte-targeting antisense oligonucleotides" Bioorganic & Medicinal Chemistry, 2016, pp. 26-32, vol. 24.
International Preliminary Report on Patentability for PCT/JP2018/020081 dated Nov. 26, 2019.

(Continued)

*Primary Examiner* — Tracy Vivlemore
(74) *Attorney, Agent, or Firm* — Knobbe Martens Olson Bear LLP

(57) ABSTRACT

Provided is an oligonucleotide conjugate comprising an oligonucleotide and two or more linearly connected asialoglycoprotein receptor-binding molecules attached to the oligonucleotide, wherein the oligonucleotide comprises a locked nucleoside analog having a bridging structure between the 4' and 2' positions, is complementary to a human PCSK9 gene, and has inhibitory activity on the expression of the human PCSK9 gene. The oligonucleotide conjugate of the present invention can be used in the field of pharmaceutical products, in particular, the field of the development and production of therapeutic agents for diseases associated with a high LDL cholesterol level.

12 Claims, 8 Drawing Sheets
Specification includes a Sequence Listing.

(56) References Cited

OTHER PUBLICATIONS

International Search Report for PCT/JP2018/020081 dated Aug. 21, 2018.
Registry (STN), Reg.No. 1580356-55-3, Apr. 4, 2014.
Registry (STN), Reg.No. 1571345-82-8, Mar. 21, 2014.
Registry (STN), Reg.No. 2037941-57-2, Nov. 25, 2016.
Rajeev, Kallanthottathil G. et al., "Hepatocyte-Specific Delivery of siRNAs Conjugated to Novel Non-nucleosidic Trivalent N-Acetylgalactosamine Elicits Robust Gene Silencing in Vivo" ChemBioChem, 2015, pp. 903-908 vol. 16.
Wada, Fumito et al., "Cholesterol-GalNAc Dual Conjugation Strategy for Reducing Renal Distribution of Antisense Oligonucleotides" Nucleic Acid Therapeutics, 2018, pp. 50-57, vol. 28, No. 1.
Yamamoto, Tsuyoshi et al., "Effect of modular conjugation strategy for N-acetylgalactosamine-targeted antisense oligonucleotides" Nucleosides, Nucleotides and Nucleic Acids, 2020, pp. 109-118, vol. 39, Nos. 1-3.
Supplementary European Search Report for EP 18805466 dated Feb. 4, 2021.

\* cited by examiner

SEQUENCE LISTING

<160> NUMBER OF SEQ ID NOS: 14

<210> SEQ ID NO 1
<211> LENGTH: 2079
<212> TYPE: DNA
<213> ORGANISM: Homo sapiens
<220> FEATURE:
<221> NAME/KEY: CDS
<222> LOCATION: (1)..(2079)

<400> SEQUENCE: 1

| | | | | | | | | | | | | | | | | |
|---|---|---|---|---|---|---|---|---|---|---|---|---|---|---|---|---|
| atg | ggc | acc | gtc | agc | tcc | agg | cgg | tcc | tgg | tgg | ccg | ctg | cca | ctg | ctg | 48 |
| Met | Gly | Thr | Val | Ser | Ser | Arg | Arg | Ser | Trp | Trp | Pro | Leu | Pro | Leu | Leu | |
| 1 | | | | 5 | | | | | 10 | | | | | 15 | | |
| ctg | ctg | ctg | ctg | ctg | ctc | ctg | ggt | ccc | gcg | ggc | gcc | cgt | gcg | cag | gag | 96 |
| Leu | Leu | Leu | Leu | Leu | Leu | Leu | Gly | Pro | Ala | Gly | Ala | Arg | Ala | Gln | Glu | |
| | | | 20 | | | | | 25 | | | | | 30 | | | |
| gac | gag | gac | ggc | gac | tac | gag | gag | ctg | gtg | cta | gcc | ttg | cgt | tcc | gag | 144 |
| Asp | Glu | Asp | Gly | Asp | Tyr | Glu | Glu | Leu | Val | Leu | Ala | Leu | Arg | Ser | Glu | |
| | | 35 | | | | | 40 | | | | | 45 | | | | |
| gag | gac | ggc | ctg | gcc | gaa | gca | ccc | gag | cac | gga | acc | aca | gcc | acc | ttc | 192 |
| Glu | Asp | Gly | Leu | Ala | Glu | Ala | Pro | Glu | His | Gly | Thr | Thr | Ala | Thr | Phe | |
| | 50 | | | | | 55 | | | | | 60 | | | | | |
| cac | cgc | tgc | gcc | aag | gat | ccg | tgg | agg | ttg | cct | ggc | acc | tac | gtg | gtg | 240 |
| His | Arg | Cys | Ala | Lys | Asp | Pro | Trp | Arg | Leu | Pro | Gly | Thr | Tyr | Val | Val | |
| 65 | | | | | 70 | | | | | 75 | | | | | 80 | |
| gtg | ctg | aag | gag | gag | acc | cac | ctc | tcg | cag | tca | gag | cgc | act | gcc | cgc | 288 |
| Val | Leu | Lys | Glu | Glu | Thr | His | Leu | Ser | Gln | Ser | Glu | Arg | Thr | Ala | Arg | |
| | | | | 85 | | | | | 90 | | | | | 95 | | |
| cgc | ctg | cag | gcc | cag | gct | gcc | cgc | cgg | gga | tac | ctc | acc | aag | atc | ctg | 336 |
| Arg | Leu | Gln | Ala | Gln | Ala | Ala | Arg | Arg | Gly | Tyr | Leu | Thr | Lys | Ile | Leu | |
| | | | 100 | | | | | 105 | | | | | 110 | | | |
| cat | gtc | ttc | cat | ggc | ctt | ctt | cct | ggc | ttc | ctg | gtg | aag | atg | agt | ggc | 384 |
| His | Val | Phe | His | Gly | Leu | Leu | Pro | Gly | Phe | Leu | Val | Lys | Met | Ser | Gly | |
| | | | 115 | | | | | 120 | | | | | 125 | | | |
| gac | ctg | ctg | gag | ctg | gcc | ttg | aag | ttg | ccc | cat | gtc | gac | tac | atc | gag | 432 |
| Asp | Leu | Leu | Glu | Leu | Ala | Leu | Lys | Leu | Pro | His | Val | Asp | Tyr | Ile | Glu | |
| | 130 | | | | | 135 | | | | | 140 | | | | | |
| gag | gac | tcc | tct | gtc | ttt | gcc | cag | agc | atc | ccg | tgg | aac | ctg | gag | cgg | 480 |
| Glu | Asp | Ser | Ser | Val | Phe | Ala | Gln | Ser | Ile | Pro | Trp | Asn | Leu | Glu | Arg | |
| 145 | | | | | 150 | | | | | 155 | | | | | 160 | |
| att | acc | cct | cca | cgg | tac | cgg | gcg | gat | gaa | tac | cag | ccc | ccc | gac | gga | 528 |
| Ile | Thr | Pro | Pro | Arg | Tyr | Arg | Ala | Asp | Glu | Tyr | Gln | Pro | Pro | Asp | Gly | |
| | | | | 165 | | | | | 170 | | | | | 175 | | |
| ggc | agc | ctg | gtg | gag | gtg | tat | ctc | cta | gac | acc | agc | ata | cag | agt | gac | 576 |
| Gly | Ser | Leu | Val | Glu | Val | Tyr | Leu | Leu | Asp | Thr | Ser | Ile | Gln | Ser | Asp | |
| | | | 180 | | | | | 185 | | | | | 190 | | | |
| cac | cgg | gaa | atc | gag | ggc | agg | gtc | atg | gtc | acc | gac | ttc | gag | aat | gtg | 624 |
| His | Arg | Glu | Ile | Glu | Gly | Arg | Val | Met | Val | Thr | Asp | Phe | Glu | Asn | Val | |
| | | | | 195 | | | | | 200 | | | | | 205 | | |
| ccc | gag | gag | gac | ggg | acc | cgc | ttc | cac | aga | cag | gcc | agc | aag | tgt | gac | 672 |
| Pro | Glu | Glu | Asp | Gly | Thr | Arg | Phe | His | Arg | Gln | Ala | Ser | Lys | Cys | Asp | |
| | | 210 | | | | | 215 | | | | | 220 | | | | |
| agt | cat | ggc | acc | cac | ctg | gca | ggg | gtg | gtc | agc | ggc | cgg | gat | gcc | ggc | 720 |
| Ser | His | Gly | Thr | His | Leu | Ala | Gly | Val | Val | Ser | Gly | Arg | Asp | Ala | Gly | |
| 225 | | | | | 230 | | | | | 235 | | | | | 240 | |
| gtg | gcc | aag | ggt | gcc | agc | atg | cgc | agc | ctg | cgc | gtg | ctc | aac | tgc | caa | 768 |
| Val | Ala | Lys | Gly | Ala | Ser | Met | Arg | Ser | Leu | Arg | Val | Leu | Asn | Cys | Gln | |
| | | | | 245 | | | | | 250 | | | | | 255 | | |
| ggg | aag | ggc | acg | gtt | agc | ggc | acc | ctc | ata | ggc | ctg | gag | ttt | att | cgg | 816 |
| Gly | Lys | Gly | Thr | Val | Ser | Gly | Thr | Leu | Ile | Gly | Leu | Glu | Phe | Ile | Arg | |

-continued

```
                260                 265                 270
aaa agc cag ctg gtc cag cct gtg ggg cca ctg gtg gtg ctg ctg ccc      864
Lys Ser Gln Leu Val Gln Pro Val Gly Pro Leu Val Val Leu Leu Pro
        275                 280                 285 ctg gcg ggt ggg tac agc cgc gtc ctc aac gcc gcc tgc cag cgc ctg      912
Leu Ala Gly Gly Tyr Ser Arg Val Leu Asn Ala Ala Cys Gln Arg Leu
    290                 295                 300 gcg agg gct ggg gtc gtg ctg gtc acc gct gcc ggc aac ttc cgg gac      960
Ala Arg Ala Gly Val Val Leu Val Thr Ala Ala Gly Asn Phe Arg Asp
305                 310                 315                 320 gat gcc tgc ctc tac tcc cca gcc tca gct ccc gag gtc atc aca gtt     1008
Asp Ala Cys Leu Tyr Ser Pro Ala Ser Ala Pro Glu Val Ile Thr Val
                325                 330                 335 ggg gcc acc aat gcc caa gac cag ccg gtg acc ctg ggg act ttg ggg     1056
Gly Ala Thr Asn Ala Gln Asp Gln Pro Val Thr Leu Gly Thr Leu Gly
            340                 345                 350 acc aac ttt ggc cgc tgt gtg gac ctc ttt gcc cca ggg gag gac atc     1104
Thr Asn Phe Gly Arg Cys Val Asp Leu Phe Ala Pro Gly Glu Asp Ile
        355                 360                 365 att ggt gcc tcc agc gac tgc agc acc tgc ttt gtg tca cag agt ggg     1152
Ile Gly Ala Ser Ser Asp Cys Ser Thr Cys Phe Val Ser Gln Ser Gly
    370                 375                 380 aca tca cag gct gct gcc cac gtg gct ggc att gca gcc atg atg ctg     1200
Thr Ser Gln Ala Ala Ala His Val Ala Gly Ile Ala Ala Met Met Leu
385                 390                 395                 400 tct gcc gag ccg gag ctc acc ctg gcc gag ttg agg cag aga ctg atc     1248
Ser Ala Glu Pro Glu Leu Thr Leu Ala Glu Leu Arg Gln Arg Leu Ile
                405                 410                 415 cac ttc tct gcc aaa gat gtc atc aat gag gcc tgg ttc cct gag gac     1296
His Phe Ser Ala Lys Asp Val Ile Asn Glu Ala Trp Phe Pro Glu Asp
            420                 425                 430 cag cgg gta ctg acc ccc aac ctg gtg gcc gcc ctg ccc ccc agc acc     1344
Gln Arg Val Leu Thr Pro Asn Leu Val Ala Ala Leu Pro Pro Ser Thr
        435                 440                 445 cat ggg gca ggt tgg cag ctg ttt tgc agg act gta tgg tca gca cac     1392
His Gly Ala Gly Trp Gln Leu Phe Cys Arg Thr Val Trp Ser Ala His
    450                 455                 460 tcg ggg cct aca cgg atg gcc aca gcc gtc gcc cgc tgc gcc cca gat     1440
Ser Gly Pro Thr Arg Met Ala Thr Ala Val Ala Arg Cys Ala Pro Asp
465                 470                 475                 480 gag gag ctg ctg agc tgc tcc agt ttc tcc agg agt ggg aag cgg cgg     1488
Glu Glu Leu Leu Ser Cys Ser Ser Phe Ser Arg Ser Gly Lys Arg Arg
                485                 490                 495 ggc gag cgc atg gag gcc caa ggg ggc aag ctg gtc tgc cgg gcc cac     1536
Gly Glu Arg Met Glu Ala Gln Gly Gly Lys Leu Val Cys Arg Ala His
            500                 505                 510 aac gct ttt ggg ggt gag ggt gtc tac gcc att gcc agg tgc tgc ctg     1584
Asn Ala Phe Gly Gly Glu Gly Val Tyr Ala Ile Ala Arg Cys Cys Leu
        515                 520                 525 cta ccc cag gcc aac tgc agc gtc cac aca gct cca cca gct gag gcc     1632
Leu Pro Gln Ala Asn Cys Ser Val His Thr Ala Pro Pro Ala Glu Ala
    530                 535                 540 agc atg ggg acc cgt gtc cac tgc cac caa cag ggc cac gtc ctc aca     1680
Ser Met Gly Thr Arg Val His Cys His Gln Gln Gly His Val Leu Thr
545                 550                 555                 560 ggc tgc agc tcc cac tgg gag gtg gag gac ctt ggc acc cac aag ccg     1728
Gly Cys Ser Ser His Trp Glu Val Glu Asp Leu Gly Thr His Lys Pro
                565                 570                 575 cct gtg ctg agg cca cga ggt cag ccc aac cag tgc gtg ggc cac agg     1776
```

-continued

```
                Pro Val Leu Arg Pro Arg Gly Gln Pro Asn Gln Cys Val Gly His Arg
                                    580                 585                 590 gag gcc agc atc cac gct tcc tgc tgc cat gcc cca ggt ctg gaa tgc              1824
Glu Ala Ser Ile His Ala Ser Cys Cys His Ala Pro Gly Leu Glu Cys
            595                 600                 605 aaa gtc aag gag cat gga atc ccg gcc cct cag gag cag gtg acc gtg              1872
Lys Val Lys Glu His Gly Ile Pro Ala Pro Gln Glu Gln Val Thr Val
610                 615                 620 gcc tgc gag gag ggc tgg acc ctg act ggc tgc agt gcc ctc cct ggg              1920
Ala Cys Glu Glu Gly Trp Thr Leu Thr Gly Cys Ser Ala Leu Pro Gly
625                 630                 635                 640 acc tcc cac gtc ctg ggg gcc tac gcc gta gac aac acg tgt gta gtc              1968
Thr Ser His Val Leu Gly Ala Tyr Ala Val Asp Asn Thr Cys Val Val
                645                 650                 655 agg agc cgg gac gtc agc act aca ggc agc acc agc gaa ggg gcc gtg              2016
Arg Ser Arg Asp Val Ser Thr Thr Gly Ser Thr Ser Glu Gly Ala Val
            660                 665                 670 aca gcc gtt gcc atc tgc tgc cgg agc cgg cac ctg gcg cag gcc tcc              2064
Thr Ala Val Ala Ile Cys Cys Arg Ser Arg His Leu Ala Gln Ala Ser
        675                 680                 685 cag gag ctc cag tga                                                          2079
Gln Glu Leu Gln
    690
```

<210> SEQ ID NO 2
<211> LENGTH: 692
<212> TYPE: PRT
<213> ORGANISM: Homo sapiens

<400> SEQUENCE: 2

```
Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
```

-continued

```
                210                 215                 220
Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
                275                 280                 285

Leu Ala Gly Gly Tyr Ser Arg Val Leu Asn Ala Ala Cys Gln Arg Leu
        290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
                355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
                435                 440                 445

His Gly Ala Gly Trp Gln Leu Phe Cys Arg Thr Val Trp Ser Ala His
        450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
                515                 520                 525

Leu Pro Gln Ala Asn Cys Ser Val His Thr Ala Pro Pro Ala Glu Ala
        530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
                580                 585                 590

Glu Ala Ser Ile His Ala Ser Cys Cys His Ala Pro Gly Leu Glu Cys
                595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
625                 630                 635                 640
```

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
        660                 665                 670

Thr Ala Val Ala Ile Cys Cys Arg Ser Arg His Leu Ala Gln Ala Ser
    675                 680                 685

Gln Glu Leu Gln
    690

<210> SEQ ID NO 3
<211> LENGTH: 14
<212> TYPE: DNA
<213> ORGANISM: Homo sapiens

<400> SEQUENCE: 3
ggacccagga gcag                                                        14

<210> SEQ ID NO 4
<211> LENGTH: 14
<212> TYPE: DNA
<213> ORGANISM: Homo sapiens

<400> SEQUENCE: 4
gaggtatccc cggc                                                        14

<210> SEQ ID NO 5
<211> LENGTH: 14
<212> TYPE: DNA
<213> ORGANISM: Homo sapiens

<400> SEQUENCE: 5
ccatgaccct gccc                                                        14

<210> SEQ ID NO 6
<211> LENGTH: 14
<212> TYPE: DNA
<213> ORGANISM: Homo sapiens

<400> SEQUENCE: 6
ctgtcacact tgct                                                        14

<210> SEQ ID NO 7
<211> LENGTH: 14
<212> TYPE: DNA
<213> ORGANISM: Homo sapiens

<400> SEQUENCE: 7
cggctgtacc cacc                                                        14

<210> SEQ ID NO 8
<211> LENGTH: 14
<212> TYPE: DNA
<213> ORGANISM: Homo sapiens

<400> SEQUENCE: 8
gatgtcctcc cctg                                                        14

<210> SEQ ID NO 9
<211> LENGTH: 14
<212> TYPE: DNA
<213> ORGANISM: Homo sapiens

```
<400> SEQUENCE: 9
gtgacacaaa gcag                                              14

<210> SEQ ID NO 10
<211> LENGTH: 14
<212> TYPE: DNA
<213> ORGANISM: Homo sapiens

<400> SEQUENCE: 10
atgccagcca cgtg                                              14

<210> SEQ ID NO 11
<211> LENGTH: 14
<212> TYPE: DNA
<213> ORGANISM: Homo sapiens

<400> SEQUENCE: 11
agctgccaac ctgc                                              14

<210> SEQ ID NO 12
<211> LENGTH: 14
<212> TYPE: DNA
<213> ORGANISM: Homo sapiens

<400> SEQUENCE: 12
gagtgtgctg acca                                              14

<210> SEQ ID NO 13
<211> LENGTH: 14
<212> TYPE: DNA
<213> ORGANISM: Homo sapiens

<400> SEQUENCE: 13
ctggcctccc tgtg                                              14

<210> SEQ ID NO 14
<211> LENGTH: 14
<212> TYPE: DNA
<213> ORGANISM: Homo sapiens

<400> SEQUENCE: 14
gcattccaga cctg                                              14
```

ANTISENSE NUCLEIC ACID TARGETING PCSK9

CROSS REFERENCE TO RELATED APPLICATIONS

This application is a U.S. National Phase application of PCT International Application Number PCT/JP2018/020081, filed on May 24, 2018, designating the United States of America and published in the Japanese language, which is an International Application of and claims the benefit of priority to Japanese Patent Application No. 2017-105121, filed on May 26, 2017. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-IWAT015-002APC.txt, the date of creation of the ASCII text file is Oct. 30, 2019, and the size of the ASCII text file is 18 KB.

TECHNICAL FIELD

The present invention relates to an antisense nucleic acid targeting PCSK9 and a pharmaceutical composition comprising the same.

BACKGROUND ART

Familial hypercholesterolemia (FH) is a condition characterized by hyper-LDL-cholesterolemia, which causes early onset and progression of atherosclerosis, often leading to the development of arteriosclerotic diseases such as myocardial infarction. For the treatment of FH, for example, lipid-lowering agents such as statins are used to control LDL-C.

Statins inhibit cholesterol synthesis, resulting in increased LDL receptor activity and LDL-C level reduction; however statins upregulate the expression of PCSK9, which is responsible for LDL receptor degradation. For this reason, standard therapy using statins or ezetimibe is not sufficiently effective for severe hypercholesterolemia such as FH and cannot prevent the progression of atherosclerosis, and thus there are not a few cases in which cardiovascular events repeatedly occur even during therapy. To patients with severe hypercholesterolemia or a type of FH refractory to medication alone, a therapy called LDL apheresis has been provided. However, this therapy imposes heavy physical and temporal burden to the patients.

A study showed that, in carriers of a loss-of-function PCSK9 variant, a lower LDL-C level and an 88% lower incidence rate of coronary artery disease were observed as compared with those in noncarriers (see Non Patent Literature 1). This finding indicates that PCSK9 is a promising target molecule of dyslipidemia. However, PCSK9 has no active center, which is an obstacle to the development of small molecule compounds serving as PCSK9 inhibitors. Under such circumstances, a novel form of PCSK9 synthesis inhibitor, namely, a PCSK9 antisense nucleic acid, is being actively researched rather than inhibitors directly acting on PCSK9.

For example, Patent Literature 1 discloses an about 10- to 30-mer antisense oligonucleotide against the human PCSK9 gene, which antisense oligonucleotide is capable of inhibiting the expression of PCSK9. This antisense oligonucleotide can be used in the form of a conjugate in which a protein, a fatty acid chain, a sugar residue, or the like, or even a drug substance such as an antibiotic is attached to the antisense oligonucleotide.

Patent Literature 2 discloses a 10- to 22-mer antisense oligonucleotide which is capable of inhibiting the activity of PCSK9 and less nephrotoxic. Also disclosed are embodiments in which a conjugate is formed from the antisense oligonucleotide and a sterol such as cholesterol or a carbohydrate such as N-acetylgalactosamine (GalNAc). In particular, tri-antennary GalNAc-conjugated antisense oligonucleotides are preferred in terms of binding affinity for the liver.

CITATION LIST

Patent Literature

Patent Literature 1:
U.S. patent application publication No. 2012/0122954
Patent Literature 2:
WO 2014/207232

Non Patent Literature

Non Patent Literature 1:
Cohen J C, et al., N Engl J Med 2006, 354, 1264-1272.

SUMMARY OF INVENTION

Technical Problem

In some cases, antisense nucleic acids may form higher-order structures or complexes, which affect the pharmacokinetics and efficacy of the antisense nucleic acids. Therefore, in order to enhance the activity of antisense nucleic acids in the body, pharmacokinetic properties of the antisense nucleic acids have to be taken into consideration.

In addition, although antisense nucleic acids are potentially useful pharmaceutical materials, those with low activity and poor tissue specificity may cause unexpected adverse effects. In fact, SPC5001, which had been under development as an antisense nucleic acid inhibitor of PCSK9, caused damage to the kidney, which was a non-target tissue, in the phase I trial conducted on healthy volunteers, and for this reason, its development was terminated (see van Poelgeest E P, et al., Am J Kidney Dis 2013, 62, 796-800; and van Poelgeest E P, et al., Br J Clin Pharmacol 2015, 80, 1350-1361). Therefore, for clinical application of antisense nucleic acids targeting PCSK9, there is a need for improvement of their tissue specificity.

The present invention provides an antisense nucleic acid which targets PCSK9 and has in vivo efficacy and low toxicity and also provides a pharmaceutical composition comprising the same.

Solution to Problem

Generally, the activity of an antisense nucleic acid is evaluated from the measurement of target mRNA reduction by the antisense nucleic acid introduced into cells with a cationic lipid-based reagent, such as Lipofectamine (by lipofection). However, this method cannot always evaluate the precise activity of the antisense nucleic acid. One reason is that the efficiency of complexation of the reagent with the antisense nucleic acid may vary with its sequence. Another reason is that this method may abolish pharmacokinetic properties inherent to the sequence of the antisense nucleic acid.

The present inventors conducted extensive research and found that antisense nucleic acids of PCSK9 which are efficacious in vivo and less toxic can be prepared by designing nucleic acid sequences with high biostability, selecting those with high binding affinity for a PCSK9 gene using a technique called the $Ca^{2+}$ enrichment of medium (CEM) method, and modifying the selected nucleic acid sequences with a specific sugar residue. Based on this finding, the present inventors completed the present invention.

That is, the present invention relates to the following. [1] An oligonucleotide conjugate comprising an oligonucleotide and two or more linearly connected asialoglycoprotein receptor-binding molecules attached to the oligonucleotide, wherein the oligonucleotide comprises a locked nucleoside analog having a bridging structure between the 4' and 2' positions, is complementary to a human PCSK9 gene, and has inhibitory activity on expression of the human PCSK9 gene.
[2] The oligonucleotide conjugate according to the above [1], wherein the bridging structure is selected from the following (i) to (iv):
(i) a structure represented by —$CH_2$—O— or —$(CH_2)_2$—O—;
(ii) a structure represented by —$CH_2$—$NR^1$—O— or —$(CH_2)_2$—$NR^1$—O—;
(iii) a structure represented by —CO—$NR^1$—, —$CH_2$—CO—$NR^1$—, —$(CH_2)_2$—CO—$NR^1$—, —CO—$NR^1$—X—, or —$CH_2$—CO—$NR^1$—X—; and
(iv) a structure represented by —$CH_2$—$NR^1$— or —$(CH_2)_2$—$NR^1$— (wherein $R^1$ represents a hydrogen atom;
an optionally branched or cyclic alkyl group of 1 to 7 carbon atoms;
an optionally branched or cyclic alkenyl group of 2 to 7 carbon atoms;
an aryl group of 3 to 12 carbon atoms which may have a heteroatom and may have any one or more substituting groups selected from group X consisting of a hydroxyl group, a straight-chain alkyl group of 1 to 6 carbon atoms, a straight-chain alkoxy group of 1 to 6 carbon atoms, a mercapto group, a straight-chain alkylthio group of 1 to 6 carbon atoms, an amino group, a straight-chain alkylamino group of 1 to 6 carbon atoms, and a halogen atom; or an alkyl group having an aryl moiety of 3 to 12 carbon atoms which moiety may have a heteroatom and may have any one or more substituting groups selected from the group a, and X represents an oxygen atom, a sulfur atom, an amino group, or a methylene group).
[3] The oligonucleotide conjugate according to the above [1] or [2], wherein the human PCSK9 gene is a region represented by a nucleotide sequence comprising any of the following: the nucleotide sequence of SEQ ID NO: 3; the nucleotide sequence of SEQ ID NO: 4; the nucleotide sequence of SEQ ID NO: 5; the nucleotide sequence of SEQ ID NO: 6; the nucleotide sequence of SEQ ID NO: 7; the nucleotide sequence of SEQ ID NO: 8; the nucleotide sequence of SEQ ID NO: 9; the nucleotide sequence of SEQ ID NO: 10; the nucleotide sequence of SEQ ID NO: 11; the nucleotide sequence of SEQ ID NO: 12; the nucleotide sequence of SEQ ID NO: 13; the nucleotide sequence of SEQ ID NO: 14; and complementary nucleotide sequences thereof.
[4] The oligonucleotide conjugate according to any of the above [1] to [3], wherein one or more internucleoside linkages are phosphorothioate linkages.
[5] The oligonucleotide conjugate according to any of the above [1] to [4], wherein one or more linkages selected from a linkage between the asialoglycoprotein receptor-binding molecules and a linkage between the oligonucleotide and the asialoglycoprotein receptor-binding molecules are phosphodiester linkages.
[6] The oligonucleotide conjugate according to any of the above [1] to [5], wherein the linkage between the oligonucleotide and the asialoglycoprotein receptor-binding molecules is a linkage via a linker selected from the following (A) and (B).

[Chem. 1]

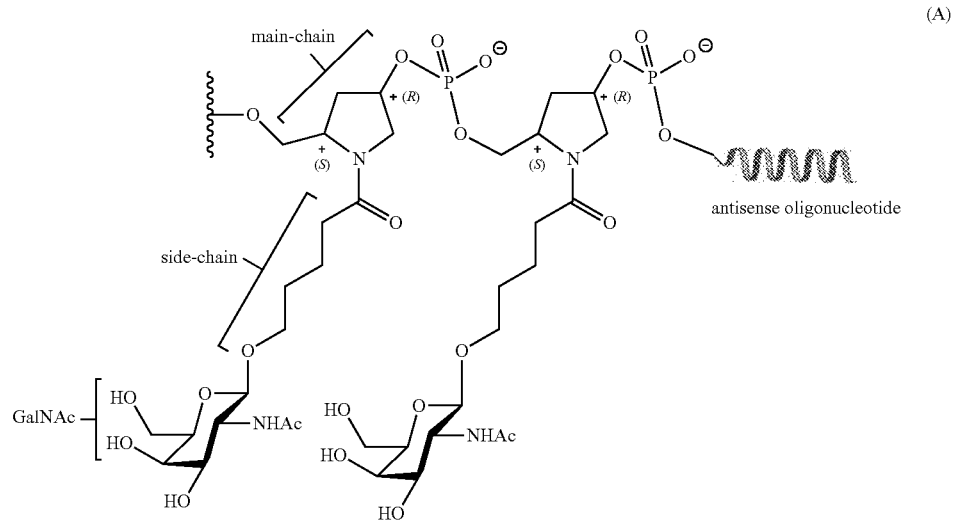

-continued

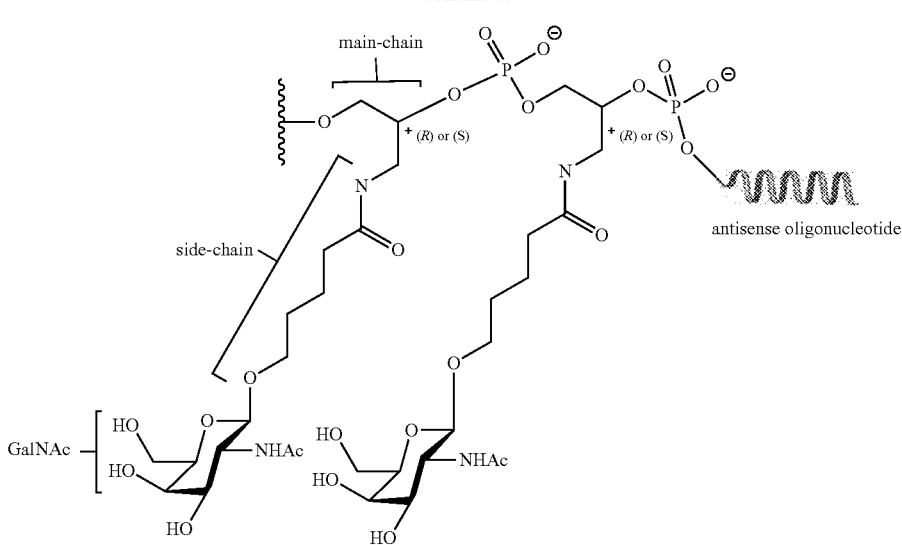

(B)

[7] The oligonucleotide conjugate according to any of the above [1] to [6], wherein the number of the asialoglycoprotein receptor-binding molecules linearly connected is 2 to 5.
[8] The oligonucleotide conjugate according to any of the above [1] to [7], wherein the asialoglycoprotein receptor-binding molecules are one or more types of molecules selected from the group consisting of lactose, galactose, N-acetylgalactosamine (GalNAc), galactosamine, N-formylgalactosamine, N-propionylgalactosamine, N-n-butanoylgalactosamine, N-iso-butanoylgalactosamine, and derivatives thereof.
[9] The oligonucleotide conjugate according to any of the above [1] to [8], wherein the oligonucleotide has a 10- to 25-base nucleotide sequence.
[10] A preventive or therapeutic agent for a disease associated with a high LDL cholesterol level, the preventive or therapeutic agent comprising the oligonucleotide conjugate according to any of the above [1] to [9] as an active ingredient.
[11] The preventive or therapeutic agent according to the above [10], wherein the disease associated with a high LDL cholesterol level is selected from hypercholesterolemia and high-risk diseases in more need of LDL cholesterol reduction.
[12] The preventive or therapeutic agent according to the above [10] or [11], wherein the preventive or therapeutic agent is an injectable preparation.

Advantageous Effects of Invention

The antisense nucleic acid of the present invention has great advantages in that it is capable of inhibiting PCSK9 expression in vivo and is less toxic, and thus is useful as a therapeutic agent for a disease associated with a high LDL cholesterol level.

DESCRIPTION OF EMBODIMENTS

Figure 1:
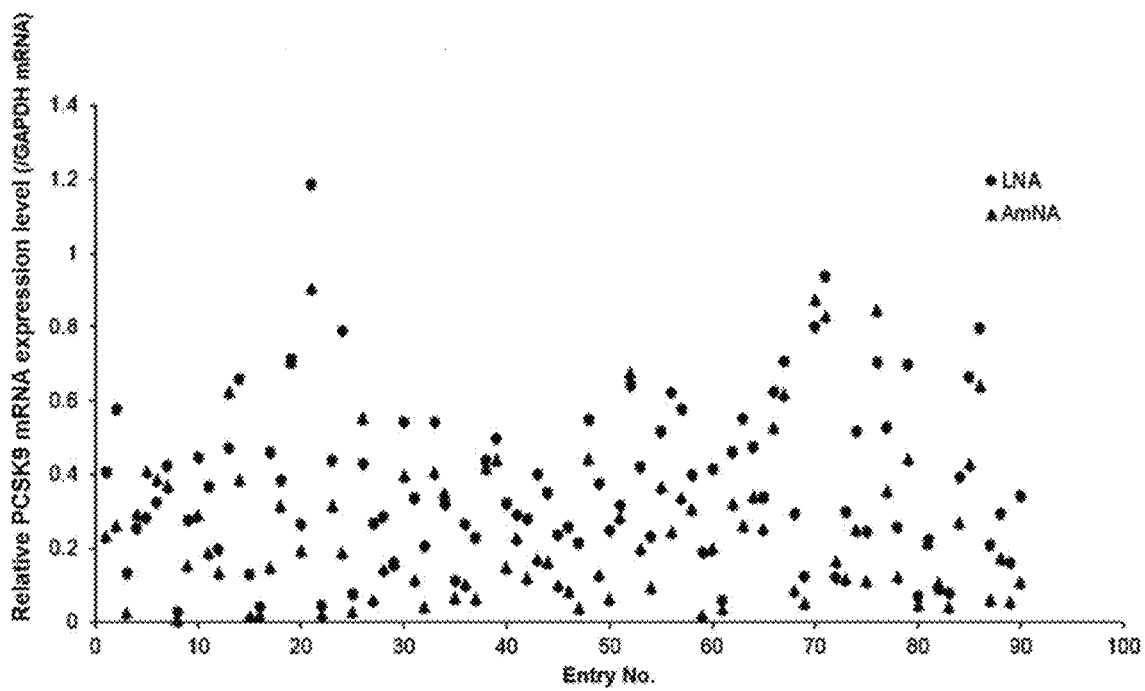
FIG. 1 shows the results of primary screening for antisense activity using the CEM method.

The antisense nucleic acid of the present invention comprises an oligonucleotide and two or more linearly connected asialoglycoprotein receptor-binding molecules attached to the oligonucleotide, wherein the oligonucleotide comprises a locked nucleoside analog having a bridging structure between the 4' and 2' positions, is complementary to a human PCSK9 gene, and has inhibitory activity on the expression of the human PCSK9 gene. Hereinafter, the antisense nucleic acid having the above-mentioned characteristics may be referred to as an oligonucleotide conjugate of the present invention or an oligonucleotide conjugate.

Various studies have been performed on modification of nucleic acids by asialoglycoprotein (ASGP) receptor-binding molecules for liver-targeting delivery of the nucleic acids. This approach is based on the finding that, taking N-acetylgalactosamine (GalNAc) as an example, three GalNAc units bind to an ASGP receptor on hepatic parenchymal cells while maintaining a specific conformation. Therefore, in order that the specific conformation can be maintained, nucleic acids are usually modified by conjugation with tri-antennary GalNAc (three GalNAc units each attached to the same point). However, in the present invention, even nucleic acids modified by conjugation with linearly connected ASGP receptor-binding molecules are shown to be sufficiently incorporated into hepatic parenchymal cells and exert favorable actions in vivo. The precise mechanism of this effect is unclear, but possible explanations include the following. Due to the linear connection of the ASGP receptor-binding molecules, the linker structure between the ASGP receptor-binding molecules and the oligonucleotide is highly flexible; each of the connected ASGP receptor-binding molecules can flexibly fit in a spatially advantageous position of the ASGP receptor; and the pattern of metabolic transformation is advantageous for exerting the activity of the oligonucleotide. This can give rise to improved efficiency of uptake of the conjugates into the target cells, which together with high biostability of the conjugates can contribute to enhanced inhibitory effect on the target gene expression, namely, human PCSK9 gene expression. However, the putative mechanism described above should not be construed as limiting the present invention.

The terms used herein will be defined as follows.

As used herein, the term "straight-chain alkyl group of 1 to 6 carbon atoms" usually refers to a straight-chain alkyl group of 1 to 6 carbon atoms, for example, a methyl group, an ethyl group, a n-propyl group, a n-butyl group, a n-pentyl group, a n-hexyl group, or the like.

As used herein, the term "straight-chain alkoxy group of 1 to 6 carbon atoms" usually includes alkoxy groups having a straight-chain alkyl group of 1 to 6 carbon atoms. For example, a methyloxy group, an ethyloxy group, a n-propyloxy group, etc. are included.

As used herein, the term "straight-chain alkylthio group of 1 to 6 carbon atoms" usually includes alkylthio groups having a straight-chain alkyl group of 1 to 6 carbon atoms. For example, a methylthio group, an ethylthio group, a n-propylthio group, etc. are included.

As used herein, the term "straight-chain alkylamino group of 1 to 6 carbon atoms" usually includes alkylamino groups having one or two straight-chain alkyl groups of 1 to 6 carbon atoms. For example, a methylamino group, a dimethylamino group, an ethylamino group, a methylethylamino group, a diethylamino group, etc. are included.

As used herein, the term "optionally branched or cyclic alkyl group of 1 to 7 carbon atoms" usually includes straight-chain alkyl groups of 1 to 7 carbon atoms, branched-chain alkyl groups of 3 to 7 carbon atoms, and cyclic alkyl groups of 3 to 7 carbon atoms. These may be collectively referred to simply as "a lower alkyl group". Examples of the straight-chain alkyl group of 1 to 7 carbon atoms include a methyl group, an ethyl group, a n-propyl group, a n-butyl group, a n-pentyl group, a n-hexyl group, and a n-heptyl group. Examples of the branched-chain alkyl group of 3 to 7 carbon atoms include an isopropyl group, an isobutyl group, a tert-butyl group, an isopentyl group, etc. Examples of the cyclic alkyl group of 3 to 7 carbon atoms include a cyclobutyl group, a cyclopentyl group, a cyclohexyl group, etc.

As used herein, the term "optionally branched or cyclic alkenyl group of 2 to 7 carbon atoms" usually includes straight-chain alkenyl groups of 2 to 7 carbon atoms, branched-chain alkenyl groups of 3 to 7 carbon atoms, and cyclic alkenyl groups of 3 to 7 carbon atoms. These may be collectively referred to simply as "a lower alkenyl group". Examples of the straight-chain alkenyl group of 2 to 7 carbon atoms include an ethenyl group, a 1-propenyl group, a 2-propenyl group, a 1-butenyl group, a 2-butenyl group, a 1-pentenyl group, a 2-pentenyl group, a 3-pentenyl group, a 4-pentenyl group, a 1-hexenyl group, etc. Examples of the branched-chain alkenyl group of 3 to 7 carbon atoms include an isopropenyl group, a 1-methyl-1-propenyl group, a 1-methyl-2-propenyl group, a 2-methyl-1-propenyl group, a 2-methyl-2-propenyl group, a 1-methyl-2-butenyl group, etc. Examples of the cyclic alkenyl group of 3 to 7 carbon atoms include a cyclobutenyl group, a cyclopentenyl group, a cyclohexenyl group, etc.

As used herein, the term "aryl group of 3 to 12 carbon atoms which may have a heteroatom" usually includes aromatic hydrocarbons of 6 to 12 carbon atoms composed of a hydrocarbon alone and heteroaromatic compounds of 3 to 12 carbon atoms having a heteroatom (a nitrogen atom, an oxygen atom, a sulfur atom) in the ring structure. Examples of the aromatic hydrocarbon of 6 to 12 carbon atoms composed of a hydrocarbon alone include a phenyl group, a naphthyl group, an indenyl group, an azulenyl group, etc. Examples of the heteroaromatic compound of 3 to 12 carbon atoms having a heteroatom in the ring structure include a pyridyl group, a pyrrolyl group, a quinolyl group, an indolyl group, an imidazolyl group, a furyl group, a thienyl group, etc.

As used herein, the term "alkyl group having an aryl moiety of 3 to 12 carbon atoms which moiety may have a heteroatom" includes, for example, a benzyl group, a phenethyl group, a naphthylmethyl group, a 3-phenylpropyl group, a 2-phenylpropyl group, a 4-phenylbutyl group, a 2-phenylbutyl group, a pyridylmethyl group, an indolylmethyl group, a furylmethyl group, a thienylmethyl group, a pyrrolylmethyl group, a 2-pyridylethyl group, a 1-pyridylethyl group, a 3-thienylpropyl group, etc. The total number of carbon atoms in such an alkyl group is not particularly limited and is, for example, in the range of 4 to 18.

As used herein, the term "halogen atom" includes, for example, a fluorine atom, a chlorine atom, a bromine atom, and an iodine atom. Preferred are a fluorine atom and a chlorine atom.

As used herein, the term "nucleoside" usually means a glycosylamine comprising a nucleobase and a sugar. Examples of the nucleoside include, but are not limited to, a naturally-occurring nucleoside, an abasic nucleoside, a modified nucleoside, and a nucleoside having a pseudo-base and/or a pseudo-sugar group.

As used herein, the term "nucleotide" usually means a glycosomine comprising a nucleobase and a sugar covalently bound to a phosphate group. The nucleotide may be modified by a substituting group.

As used herein, the term "deoxyribonucleotide" usually means a nucleotide having a hydrogen atom at the 2' position of the sugar moiety of the nucleotide. The deoxyribonucleotide may be modified by a substituting group.

As used herein, the term "deoxyribonucleic acid (DNA)" usually means a nucleic acid composed of deoxyribonucleotides.

As used herein, the term "ribonucleotide" usually means a nucleotide having a hydroxyl group at the 2' position of the sugar moiety of the nucleotide. The ribonucleotide may be modified by a substituting group.

As used herein, the term "ribonucleic acid (RNA)" usually means a nucleic acid composed of ribonucleotides.

As used herein, the term "modified nucleoside" usually means an unnatural "nucleoside" in which a sugar is bound to a purine base or a pyrimidine base; and a compound in which a sugar is bound to a heteroaromatic ring or aromatic hydrocarbon ring that is neither a purine base nor a pyrimidine base and is substitutable for a purine base or a pyrimidine base. Preferred is a modified nucleoside having modification in the sugar moiety.

As used herein, the term "oligonucleotide" refers to an "oligonucleotide" having 2 to 50 identical or different "nucleosides" connected by one or more phosphodiester linkages or other internucleoside linkages. Unnatural derivatives of the "oligonucleotide" are also included. Preferable examples of such a derivative include oligonucleotide derivatives in which at least one sugar moiety is modified; oligonucleotide derivatives in which at least one phosphodiester moiety is converted to a phosphorothioate; oligonucleotide derivatives in which an oxygen atom of the phosphate group of at least one phosphodiester linkage is substituted by a sulfur atom (phosphorothioate oligonucleotides); oligonucleotide derivatives in which the terminal phosphoric acid moiety is esterified; and oligonucleotide derivatives in which the amino group of at least one purine base is amidated. The "oligonucleotide" includes a single-stranded DNA or RNA and a double-stranded DNA or RNA unless otherwise specified. Preferred is a natural or unnatural single-stranded antisense oligonucleotide. The "oligonucleotide" includes pharmaceutically acceptable salts thereof unless otherwise specified.

Next, the present invention will be described in more detail.

The oligonucleotide of the oligonucleotide conjugate of the present invention comprises a locked nucleoside analog having a bridging structure between the 4' and 2' positions. Due to the bridging structure, the oligonucleotide conjugate is resistant to degradation mediated by various nucleases and can stay in a living body for a prolonged time after administration.

An example of the bridging structure is a structure represented by —CH$_2$—O— or —(CH$_2$)$_2$—O—. Hereinafter, this bridging structure may be referred to as a bridging structure of embodiment 1 (BNA).

Examples of the bridging structure of embodiment 1 include, but are not limited to, β-L-methyleneoxy (4'-CH$_2$-O-2', this may be referred to as "LNA"), R-D-methyleneoxy (4'-CH$_2$—O-2'), and ethyleneoxy (4'-(CH$_2$)$_2$—O-2'). The BNA nucleoside (monomer) or an oligonucleotide comprising the BNA nucleosides can be synthesized by the method described in known literature, for example, WO 2011/052436.

Another example of the bridging structure is a structure represented by —CH$_2$—NR$^1$—O— or —(CH$_2$)$_2$—NR$^1$—O—. In the formula, R$^1$ represents a hydrogen atom;
an optionally branched or cyclic alkyl group of 1 to 7 carbon atoms;
an optionally branched or cyclic alkenyl group of 2 to 7 carbon atoms;
an aryl group of 3 to 12 carbon atoms which may have a heteroatom and may have any one or more substituting groups selected from group a consisting of a hydroxyl group, a straight-chain alkyl group of 1 to 6 carbon atoms, a straight-chain alkoxy group of 1 to 6 carbon atoms, a mercapto group, a straight-chain alkylthio group of 1 to 6 carbon atoms, an amino group, a straight-chain alkylamino group of 1 to 6 carbon atoms, and a halogen atom; or an alkyl group having an aryl moiety of 3 to 12 carbon atoms which moiety may have a heteroatom and may have any one or more substituting groups selected from the group a.

Hereinafter, this bridging structure may be referred to as a bridging structure of embodiment 2 (BNA$^{NC}$).

Examples of the bridging structure of embodiment 2 include, but are not limited to, oxyamino (4'-CH$_2$—NH—O-2') and N-methyloxyamino (4'-CH$_2$—NCH$_3$—O-2'). The BNA$^{NC}$ nucleoside (monomer) or an oligonucleotide comprising the BNA$^{NC}$ nucleosides can be synthesized by the method described in known literature, for example, WO 2011/052436.

Yet another example of the bridging structure is a structure represented by —CO—NR$^1$—, —CH$_2$—CO—NR$^1$—, —(CH$_2$)$_2$—CO—NR$^1$—, —CO—NR$^1$—X—, or —CH$_2$—CO—NR$^1$—X—. In the formula, R$^1$ represents a hydrogen atom;
an optionally branched or cyclic alkyl group of 1 to 7 carbon atoms;
an optionally branched or cyclic alkenyl group of 2 to 7 carbon atoms;
an aryl group of 3 to 12 carbon atoms which may have a heteroatom and may have any one or more substituting groups selected from group a consisting of a hydroxyl group, a straight-chain alkyl group of 1 to 6 carbon atoms, a straight-chain alkoxy group of 1 to 6 carbon atoms, a mercapto group, a straight-chain alkylthio group of 1 to 6 carbon atoms, an amino group, a straight-chain alkylamino group of 1 to 6 carbon atoms, and a halogen atom; or an alkyl group having an aryl moiety of 3 to 12 carbon atoms which moiety may have a heteroatom and may have any one or more substituting groups selected from the group a, and X represents an oxygen atom, a sulfur atom, an amino group, or a methylene group.

Hereinafter, this bridging structure may be referred to as a bridging structure of embodiment 3 (AmNA).

Examples of the bridging structure of embodiment 3 include, but are not limited to, non-substituted amide (4'-CO—NH-2'), N-methylamide (4'-CO—NCH$_3$-2'), acetamide (4'-CH$_2$—CO—NH-2'), N-methylacetamide (4'-CH$_2$—CO—NCH$_3$-2'), N-oxyacetamide (4'-CH$_2$—CO—NH—O-2'), and N-methyl-N-oxyacetamide (4'-CH$_2$—

CO—NCH$_3$—O-2'). The AmNA nucleoside (monomer) or an oligonucleotide comprising the AmNA nucleosides can be synthesized by the method described in known literature, for example, WO 2012/029870.

Yet still another example of the bridging structure is a structure represented by —CH$_2$—NR$^1$— or —(CH$_2$)$_2$—NR$^1$—. In the formula, R$^1$ represents a hydrogen atom; an optionally branched or cyclic alkyl group of 1 to 7 carbon atoms;
an optionally branched or cyclic alkenyl group of 2 to 7 carbon atoms;
an aryl group of 3 to 12 carbon atoms which may have a heteroatom and may have any one or more substituting groups selected from group a consisting of a hydroxyl group, a straight-chain alkyl group of 1 to 6 carbon atoms, a straight-chain alkoxy group of 1 to 6 carbon atoms, a mercapto group, a straight-chain alkylthio group of 1 to 6 carbon atoms, an amino group, a straight-chain alkylamino group of 1 to 6 carbon atoms, and a halogen atom; or an alkyl group having an aryl moiety of 3 to 12 carbon atoms which moiety may have a heteroatom and may have any one or more substituting groups selected from the group a.

Hereinafter, this bridging structure may be referred to as a bridging structure of embodiment 4.

Examples of the bridging structure of embodiment 4 include, but are not limited to, amino (4'-CH$_2$—NH-2') and N-methylamino (4'-CH$_2$—NCH$_3$-2'). A nucleoside (monomer) having the bridging structure of embodiment 4 or an oligonucleotide comprising the nucleosides can be synthesized by the method described in known literature, for example, Kumar R. et al., Bioorg. & Med. Chem. Lett., 1998, 8, 2219-2222; or Singh S. K. et al., J. Org. Chem., 1998, 63, 10035-39.

The locked nucleoside analog can be prepared by introducing any of these bridging structures into a nucleoside as the monomeric unit of an oligonucleotide. In the case where the oligonucleotide contains two or more locked nucleoside analogs, the bridging structures may be all the same or different. There is no particular limitation. That is, two or more types of bridging structures of the same embodiment may be used in combination, and two or more types of bridging structures of different embodiments may be used in combination. There is no particular limitation.

The percentage of the number of locked nucleoside analogs in the oligonucleotide used in the present invention is not particularly limited. For example, the lower limit is 5%, 7%, 10%, 15%, 20%, or 25% of the total number. In addition, the upper limit is also not particularly limited. For example, the oligonucleotide used in the present invention may be exclusively composed of locked nucleoside analogs, in other words, the percentage of the number of locked nucleoside analogs in the oligonucleotide may be 100%. Also, the upper limit may be 90%, 80%, 70%, or 60% of the total number.

The location of the locked nucleoside analog in the oligonucleotide is not particularly limited. For example, the locked nucleoside analog may be located at the 5'- or 3'-end or both ends of the oligonucleotide. Alternatively, more than one locked nucleotide analog may be located discontinuously or contiguously in the oligonucleotide. For example, two contiguous nucleosides from the 5'-end and the 2nd and 3rd nucleosides from the 3'-end may be locked nucleoside analogs.

The oligonucleotide used in the present invention is complementary to a human PCSK9 gene and capable of binding to the gene. The term "capable of binding" means that two or more different single-stranded oligonucleotides or nucleic acids can form a two or more-stranded nucleic acid due to the complementarity of base pairs between the two or more strands. Preferably, the term "capable of binding" means that two different single-stranded oligonucleotides or nucleic acids can form a double-stranded nucleic acid. The melting temperature ($T_m$) of the two or more-stranded nucleic acid is not particularly limited. For example, when two different single-stranded oligonucleotides or nucleic acids form a double-stranded nucleic acid, both the nucleotide sequences do not have to be completely complementary in the double-stranded region.

The oligonucleotide used in the present invention has inhibitory activity on human PCSK9 gene expression. More specifically, for example, the oligonucleotide used in the present invention forms a stable double-stranded structure with human PCSK9 mRNA and degrades PCSK9 mRNA and/or inhibits the biosynthesis of PCSK9 protein. In the present invention, such inhibitory activity can be measured and evaluated using a technique called the "Ca$^{2+}$ enrichment of medium (CEM) method".

The procedure for evaluation of the inhibitory activity using the CEM method is as follows. A human hepatoma cell line, Huh-7, is cultured in a usual medium for 24 hours. After that, the medium is replaced with CEM (CaCl$_2$-containing medium) containing a test oligonucleotide at 200 nM. After 24 hours, total RNA is extracted, and the expression level of PCSK9 mRNA is quantified on a real-time PCR system. A lower expression level of PCSK9 mRNA indicates that the test oligonucleotide has higher inhibitory activity on human PCSK9 gene expression.

The human PCSK9 gene comprises the nucleotide sequence of SEQ ID NO: 1 (GenBank accession number: NM_174936; coding region, 2079 bases) and encodes the amino acid sequence of SEQ ID NO: 2. The PCSK9 gene plays a role in LDL receptor degradation. As used herein, the human PCSK9 gene includes not only a gene consisting of the nucleotide sequence of SEQ ID NO: 1, but also a variant thereof which may occur in a human body, for example, a variant gene consisting of a nucleotide sequence identical to the nucleotide sequence of SEQ ID NO: 1 except for one to several base deletions, substitutions, and/or additions due to polymorphism or spontaneous mutation. Moreover, the human PCSK9 gene includes a variant consisting of a nucleotide sequence which has, for example, 80% or more, 85% or more, 90% or more, 95% or more, 97% or more, 98% or more, 99% or more, 99.5% or more, or 99.9% or more identity to the nucleotide sequence of SEQ ID NO: 1. The identity of the nucleotide sequence can be determined using a known algorithm such as BLAST or FASTA.

The region of the human PCSK9 gene to which the oligonucleotide used in the present invention is capable of binding is preferably represented by a nucleotide sequence comprising any of the following: the nucleotide sequence of SEQ ID NO: 3; the nucleotide sequence of SEQ ID NO: 4; the nucleotide sequence of SEQ ID NO: 5; the nucleotide sequence of SEQ ID NO: 6; the nucleotide sequence of SEQ ID NO: 7; the nucleotide sequence of SEQ ID NO: 8; the nucleotide sequence of SEQ ID NO: 9; the nucleotide sequence of SEQ ID NO: 10; the nucleotide sequence of SEQ ID NO: 11; the nucleotide sequence of SEQ ID NO: 12; the nucleotide sequence of SEQ ID NO: 13; the nucleotide sequence of SEQ ID NO: 14; and complementary nucleotide sequences thereof. More preferred is a DNA or RNA consisting of any of these nucleotide sequences.

The oligonucleotide used in the present invention can be synthesized by the usual method. For example, the oligonucleotide can readily be synthesized with a commercial DNA synthesizer (e.g., manufactured by Thermo Fisher Scientific, etc.). The synthesis method may be a phosphoramidite-based solid phase synthesis method, a hydrogenphosphonate-based solid phase synthesis method, or the like.

The length of the nucleotide sequence of the oligonucleotide used in the present invention is not particularly limited. For example, the oligonucleotide used in the present invention preferably has a 10- to 25-base nucleotide sequence and more preferably has a 13- to 20-base nucleotide sequence. The internucleoside linkage is, for example, a phosphodiester linkage or another type of internucleoside linkage (e.g., a phosphorothioate linkage). Preferred is a phosphorothioate linkage because it is advantageous for inhibition of PCSK9 expression.

In the present invention, the oligonucleotide conjugate is characterized in that two or more linearly connected ASGP receptor-binding molecules are attached to the 5'- or 3'-end or both ends of the oligonucleotide. The term "attached to both ends" herein means that a set of two or more linearly connected ASGP receptor-binding molecules is attached to each end. The above characteristic enables targeting delivery of the oligonucleotide conjugate of the present invention to hepatic parenchymal cells.

The ASGP receptor-binding molecule refers to a molecule capable of binding to an ASGP receptor and is, for example, an asialoglycoprotein. Specific examples of the asialoglycoprotein include lactose, galactose, N-acetylgalactosamine (GalNAc), galactosamine, N-formylgalactosamine, N-propionylgalactosamine, N-n-butanoylgalactosamine, N-isobutanoylgalactosamine, and derivatives thereof. The derivative of the asialoglycoprotein is not particularly limited as long as it is capable of binding to an ASGP receptor. Examples include derivatives of asialoglycoproteins obtained by functional group conversion etc.; and asialoglycoproteins substituted with saccharides, amino acids, vitamins, or fatty acids. Also included are low-molecular-weight compounds without a sugar backbone; monoclonal antibodies against an ASGP receptor (including monoclonal antibody fragments and antibody-like molecules such as ankyrin); and nucleic acid aptamers. The ASGP receptor-binding molecules attached to the oligonucleotide may be a single type of molecule or a combination of two or more types of molecules selected from the foregoing examples.

As long as two or more ASGP receptor-binding molecules are attached to the 5'- or 3'-end or both ends of the oligonucleotide, there is no particular limitation on the number of the ASGP receptor-binding molecules attached thereto. Preferred is 3 or more. In addition, the number of the ASGP receptor-binding molecules is preferably 10 or less, more preferably 7 or less, and still more preferably 5 or less. In the case where the ASGP receptor-binding molecules are attached to both ends of the oligonucleotide, the total number of the ASGP receptor-binding molecules attached thereto is not particularly limited and is, for example, 4 to 20. The linkage between the ASGP receptor-binding molecules is, for example, a phosphodiester linkage or a phosphorothioate linkage, but preferred is a phosphodiester linkage because the conjugate of the present invention properly undergoes intracellular metabolism that enables the oligonucleotide to efficiently act on the target mRNA.

The ASGP receptor-binding molecules may be attached to the oligonucleotide via a linker. Specifically, for example, in the case where two or more ASGP receptor-binding molecules are attached to the oligonucleotide, two or more main-chain linkers are connected and attached to the oligonucleotide; and each ASGP receptor-binding molecule is attached to a side-chain linker branched from each main-chain linker. The main-chain linker is not particularly limited and is, for example, a straight-chain or branched-chain, saturated or unsaturated carbon chain spacer. In the case where the side-chain linker contains a heteroatom as described later, the heteroatom together with some carbon atoms in the carbon chain of the main-chain linker may form a heterocycle. The length of the carbon chain is not particularly limited, but in terms of the flexibility of the ASGP receptor-binding molecules for binding to an ASGP receptor, the lower limit of the number of carbon atoms is preferably 2, and the upper limit is, for example, 18, 16, 12, 10, 8, 6, 5, or 4. Specific examples of the carbon chain include, an ethylene chain, a propylene chain, a butylene chain, an isopropylene chain, a pentylene chain, a hexylene chain, a heptylene chain, an octylene chain, a nonylene chain, a decylene chain, a dodecylene chain, a tetradecylene chain, a hexadecylene chain, an octadecylene chain, etc. The two or more main-chain linkers in the conjugate may be the same or different. The side-chain linker is also not particularly limited and is, for example, a straight-chain or branched-chain, saturated or unsaturated carbon chain spacer (optionally containing a heteroatom or a heterocycle). The length of the carbon chain is not particularly limited, and the number of carbon atoms is, for example, about 5 to 50.

The main-chain linker and the side-chain linker may be collectively referred to simply as a "linker". The linker in the present invention preferably has a highly flexible structure so that proper metabolism of the conjugate of the present invention can be facilitated within cells. In addition, the linker preferably has such a structure that each of the connected ASGP receptor-binding molecules flexibly fits in a spatially advantageous position of the ASGP receptor. The linker having such a structure allows connection of ASGP receptor-binding molecules while maintaining their individual flexibility. For example, a main-chain linker that is a straight-chain saturated carbon chain is more flexible than a main-chain linker that has a cyclic structure. The linkage between the oligonucleotide and the ASGP receptor-binding molecules, that is, the linkage between the oligonucleotide and the linker is, for example, a phosphodiester linkage or a phosphorothioate linkage, but preferred is a phosphodiester linkage because the conjugate of the present invention properly undergoes intracellular metabolism that enables the oligonucleotide to efficiently act on the target mRNA. Hereinafter, described are embodiments where a preferable linker is used for connection of the ASGP receptor-binding molecules.

(A) an embodiment in which each ASGP receptor-binding molecule bound to a butylene-based main-chain linker via a side-chain linker which is linked to the main-chain linker through a pyrrolidine ring (hereafter referred to as structure (A)); and (B) an embodiment in which each ASGP receptor-binding molecule bound to an ethylene-based main-chain linker via a side-chain linker (hereafter referred to as structure (B)).

The present invention includes embodiments where a linker structure composed of a combination of structures (A) and (B) is used.

[Chem. 2]

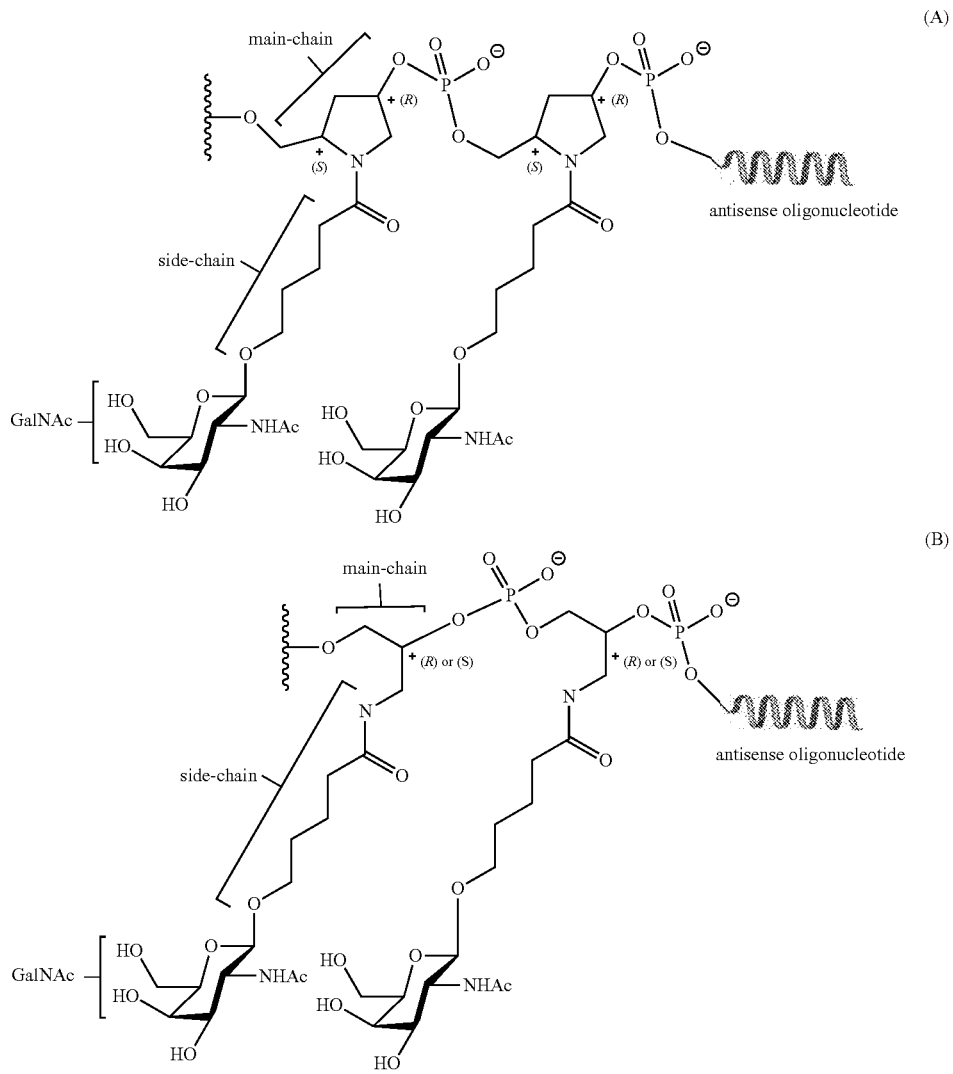

The attachment of two or more connected ASGP receptor-binding molecules to the oligonucleotide can be performed according to the method described in known literature, for example, Yamamoto T et al., Bioorg Med Chem., 2016, 24, 26-32.

In addition to terminal modification of the oligonucleotide by the ASGP receptor-binding molecules, the oligonucleotide conjugate of the present invention may have a known chemical modification of nucleotides as monomeric units. Specifically, for example, additional ASGP receptor-binding molecules and/or other functional molecules may be introduced into the 2'-nitrogen atom of AmNA, the 2'-nitrogen atom of BNA$^{NC}$, the position 5' of uracil, etc., via a known linker as needed. Such modifications can alter the activity of the oligonucleotide, for example, enhance the affinity for the target nucleic acid, increase nuclease resistance, reduce off-target toxicity, and/or alter the pharmacokinetics or tissue distribution of the oligonucleotide. The position and number of such modifications are not particularly limited and may be determined as appropriate for the purposes.

In addition to 5'- or 3'-terminal modification of the oligonucleotide by the ASGP receptor-binding molecules, the oligonucleotide conjugate of the present invention may have at least one additional component attached thereto. The at least one additional component is, for example, selected from the group consisting of sugars such as mannose, antibodies, aptamers, intercalators, reporter molecules, polyamines, polyamides, polyethylene glycols, thioethers, polyethers, cholesterols, thiocholesterols, cholic-acid moieties, folic acid, lipids, phospholipids, biotin, phenazine, phenanthridine, anthraquinone, adamantane, acridine, fluorescein, rhodamine, coumarin, and pigments. The attachment of the at least one additional component can be achieved according to a known method. The at least one additional component may be attached to the ASGP receptor-binding molecules attached to the 5'- or 3'-end of the oligonucleotide.

The oligonucleotide conjugate of the present invention can be in the form of a pharmaceutically acceptable salt, ester or ester salt, or in another derivative form which is capable of providing, either directly or indirectly, a biologically active metabolite or residue once administered to animals including humans.

The pharmaceutically acceptable salt refers to a salt of the oligonucleotide conjugate of the present invention acceptable for physiological and pharmaceutical use, namely, a salt which retains the desired biological activity of a parent compound without unwanted toxicological effects. Preferable examples of the pharmaceutically acceptable salt of an oligonucleotide and use thereof are well known to the skilled person.

Specific preferable examples of the pharmaceutically acceptable salt of an oligonucleotide include, but are not limited to, (a) salts formed with cations such as sodium, potassium, ammonium, magnesium, calcium, and polyamines such as spermine and spermidine; (b) acid addition salts formed with inorganic acids, for example, hydrochloric acid, hydrobromic acid, sulfuric acid, phosphoric acid, and nitric acid; (c) salts formed with organic acids such as acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, and polygalacturonic acid; and (d) salts formed with anions of elements such as chlorine, bromine, and iodine.

The features of the oligonucleotide conjugate of the present invention are as described above. In an exemplary embodiment, the oligonucleotide has a 14-base nucleotide sequence; two contiguous nucleosides from the 5'-end of the oligonucleotide and the 2nd and 3rd nucleosides from the 3'-end of the oligonucleotide are locked nucleoside analogs each having a bridging structure of embodiment 1; internucleoside linkages are phosphorothioate linkages; and three N-acetylgalactosamine molecules are linearly connected and attached to the 5'-end of the oligonucleotide. In this embodiment, the linkages between the three N-acetylgalactosamine molecules and the linkage between the oligonucleotide and the N-acetylgalactosamine molecules are phosphodiester linkages, and the three N-acetylgalactosamine molecules may be connected by phosphodiester linkages via linkers.

The oligonucleotide conjugate of the present invention, which has the above-described bridging structure and modification by ASGP receptor-binding molecules, can be stably incorporated into target cells and play a functional role therein. For example, the oligonucleotide conjugate can form a stable double-stranded structure with mRNA of a pathogenic protein and inhibit biosynthesis of the protein (the antisense method). Also, the oligonucleotide conjugate can form a three-stranded structure with genomic double-stranded DNA and inhibit mRNA transcription. For these reasons, the oligonucleotide conjugate of the present invention is potentially useful as a pharmaceutical product (antisense nucleic acid) that blocks the action of the PCSK9 gene for disease therapy. More specifically, for example, the oligonucleotide conjugate of the present invention is a promising antisense nucleic acid that binds to human PCSK9 mRNA and inhibits human PCSK9 gene expression. The inhibition of human PCSK9 gene expression leads to increase in LDL receptor protein expression level and subsequent enhancement in LDL cellular uptake and metabolism, resulting in reduction in blood LDL level. Thus, the oligonucleotide conjugate of the present invention serves as a dyslipidemia therapeutic agent, for example. Hereinafter, a pharmaceutical product comprising the oligonucleotide conjugate of the present invention as an active ingredient is referred to as a pharmaceutical composition of the present invention.

The pharmaceutical composition of the present invention can specifically inhibit PCSK9, and therefore, can be used as a preventive or therapeutic agent for a disease associated with a high LDL cholesterol level. Examples of the disease associated with a high LDL cholesterol level include dyslipidemia such as hypercholesterolemia including familial hypercholesterolemia. Also included are high-risk diseases in more need of LDL cholesterol reduction, such as a history of coronary artery disease, diabetes, chronic nephropathy, noncardiogenic cerebral infarction, and peripheral arterial disease.

The pharmaceutical composition of the present invention can be prepared as a parenteral preparation or a liposome preparation by blending the oligonucleotide conjugate of the present invention with an adjuvant usually used in the technical field of pharmaceutical preparations, such as a filler, a binder, a preservative, an oxidation stabilizer, a disintegrant, a lubricant, and a taste masking agent. Examples of the parenteral preparation include a transpulmonary preparation (e.g., a preparation for use with a nebulizer etc.), a transnasal preparation, a transdermal preparation (e.g., an ointment, a cream), an injectable preparation, etc. The injectable preparation can be administered locally or systemically by, for example, intravenous injection such as infusion, intramuscular injection, intraperitoneal injection, subcutaneous injection, or the like. The injectable preparation can be produced as a solution or a lyophilized preparation for reconstitution before use by blending the oligonucleotide conjugate of the present invention with a pharmaceutical carrier usually used in the technical field.

The dose of the pharmaceutical composition of the present invention may vary with the age, the sex, the symptom, the route and frequency of administration, and the dosage form. The mode of administration can be selected as appropriate for patient's age and symptom. The effective dose includes, for example, 0.01 µg to 1000 mg, 0.1 µg to 100 µg, or the like of the oligonucleotide conjugate of the present invention per administration to a human weighing 50 kg.

The individual suitable for the application of the pharmaceutical composition of the present invention is preferably a human in need of therapy for a disease associated with a high LDL cholesterol level, but is not limited thereto. For example, a pet animal in need of therapy for a disease associated with a high LDL cholesterol level is also suitable. The disease associated with a high LDL cholesterol level is as described above.

The present invention also provides the following embodiments. The specifications of the oligonucleotide conjugate of the present invention, the preparation method thereof, and the like are as described above in the section for describing the oligonucleotide conjugate of the present invention.

(I) A method for treating a disease associated with a high LDL cholesterol level, the method comprising a step of administering the oligonucleotide conjugate of the present invention.

(II) Use of the oligonucleotide conjugate of the present invention for treatment of a disease associated with a high LDL cholesterol level.

(III) Use of the oligonucleotide conjugate of the present invention for production of a therapeutic agent for a disease associated with a high LDL cholesterol level.

EXAMPLES

Hereinafter, the present invention will be described in detail with reference to examples which are illustrative only and should not be construed as limiting the invention.

Test Example 1

A human hepatoma cell line, Huh-7, was seeded on plates and cultured in DMEM (10% FBS, 1% penicillin, 1% streptomycin) for 24 hours. After that, the medium was replaced with CEM (DMEM containing 10% FBS, 1% penicillin, 1% streptomycin, and 9 mM $CaCl_2$) containing a test antisense oligonucleotide at 200 nM. After 24 hours, total RNA was extracted and then subjected to cDNA synthesis.

Gene amplification was performed on a StepOnePlus (registered trademark) real-time PCR system (ABI) using the probes shown below to quantify the expression levels of PCSK9 mRNA and GAPDH mRNA. The relative expression level of PCSK9 mRNA was then determined. For this test, a variety of antisense oligonucleotides were prepared by introducing an "LNA (4'-$CH_2$—O-2')" or "AmNA (4'-CO—$NCH_3$-2')" bridging structure into the nucleotide sequences of selected regions of the human PCSK9 gene according to a known method. The results are shown in FIG. 1.

PCSK9: Hs00545399_m1 (Thermo Fisher Scientific, Product No. 4331182)
GAPDH: Hs02786624_g1 (Thermo Fisher Scientific, Product No. 4331182)

As shown in FIG. 1, the relative expression level of PCSK9 mRNA was below 0.05 in some antisense oligonucleotides. The results demonstrate that the CEM method can be used to efficiently screen for antisense oligonucleotides having inhibitory effect on PCSK9 gene expression. The sequences of the antisense oligonucleotides shown to have inhibitory effect are specifically listed below. All the listed antisense oligonucleotides having a bridging structure, whether LNA or AmNA, showed lower relative expression levels of PCSK9 mRNA, indicating that the antisense oligonucleotides having the same sequence have similar activities regardless of the type of the bridging structure used in their sequences.

TABLE 1

| Name of oligonucleotide | Nucleotide sequence of oligonucleotide | Target region of PCSK9 gene |
|---|---|---|
| HsPCSK9-61 | 5'-GGacccaggagCAg-3 | 423-436 (SEQ ID NO: 3) |
| HsPCSK9-311 | 5'-GAggtatccccGGc-3' | 673-686 (SEQ ID NO: 4) |
| HsPCSK9-591 | 5'-CCatgaccctgCCc-3' | 953-966 (SEQ ID NO: 5) |
| HsPCSK9-661 | 5'-CTgtcacacttGCt-3' | 1023-1036 (SEQ ID NO: 6) |
| HsPCSK9-871 | 5'-CGgctgtacccACc-3' | 1233-1246 (SEQ ID NO: 7) |
| HsPCSK9-1091 | 5'-GAtgtcctcccCTg-3' | 1453-1466 (SEQ ID NO: 8) |
| HsPCSK9-1131 | 5'-GTgacacaaagCAg-3' | 1493-1506 (SEQ ID NO: 9) |
| HsPCSK9-1171 | 5'-ATgccagccacGTg-3' | 1533-1546 (SEQ ID NO: 10) |
| HsPCSK9-1351 | 5'-AGctgccaaccTGc-3' | 1713-1726 (SEQ ID NO: 11) |
| HsPCSK9-1381 | 5'-GAgtgtgctgaCCa-3' | 1743-1756 (SEQ ID NO: 12) |
| HsPCSK9-1771 | 5'-CTggcctccctGTg-3' | 2133-2146 (SEQ ID NO: 13) |
| HsPCSK9-1811 | 5'-GCattccagacCTg-3' | 2173-2186 (SEQ ID NO: 14) |

*All the internucleotide linkages are phosphorothioate linkages. The upper-case letter indicates for DNA having LNA or AmNA, and the lower-case letter indicates DNA.

Test Example 2

A human hepatoma cell line, Huh-7, was seeded on plates and cultured in DMEM (10% FBS, 1% penicillin, 1% streptomycin) for 24 hours. After that, the medium was replaced with CEM (DMEM containing 10% FBS, 1% penicillin, 1% streptomycin, and 9 mM $CaCl_2$) containing an antisense oligonucleotide at a final concentration of 8 to 200 nM. In this test, antisense oligonucleotides selected based on the results of the screening of Test Example 1 (antisense oligonucleotides having an AmNA bridging structure) were used. After 24 hours, total RNA was extracted and then subjected to cDNA synthesis. Gene amplification was performed on a StepOnePlus (registered trademark) real-time PCR system (ABI) using SYBR Green (Fast SYBR (registered trademark) Green Master Mix) and the same probes as used in Test Example 1 to determine the relative expression level of PCSK9 mRNA. The results are shown in FIG. 2.

Figure 2:
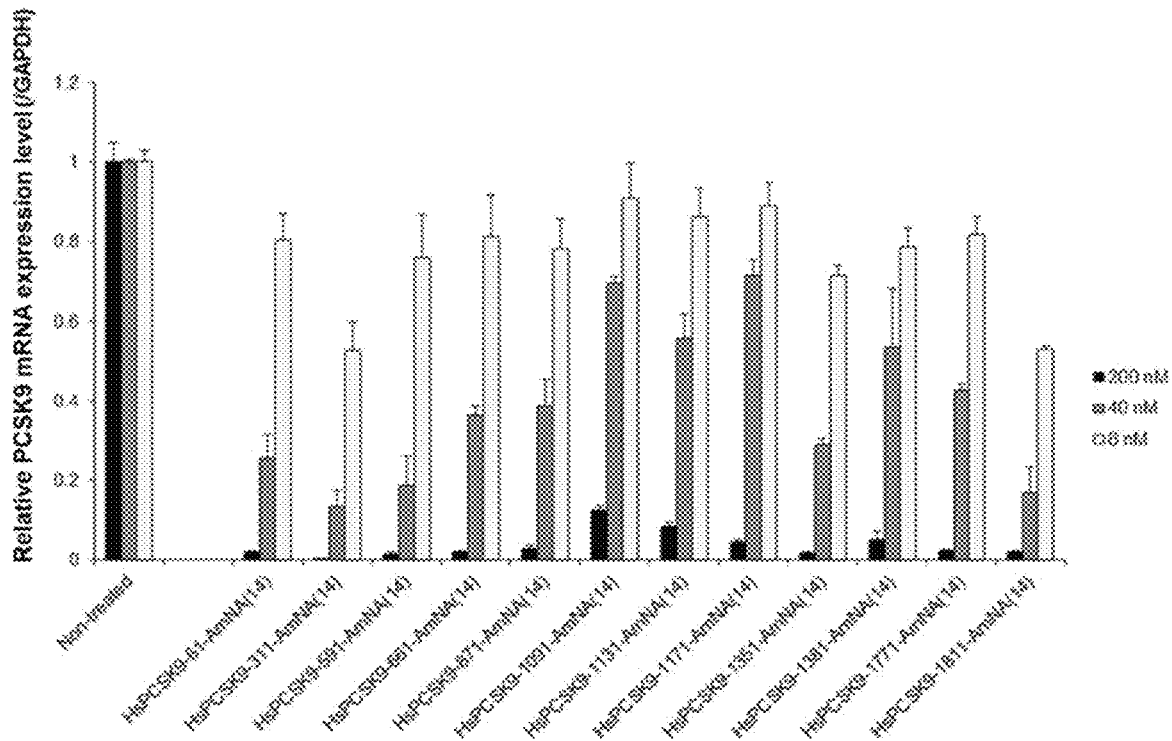
FIG. 2 shows the results of the examination of the concentration dependency of the activity of the antisense nucleic acids selected in the primary screening.

As shown in FIG. 2, the concentration dependency was confirmed in all the sequences. In particular, HsPCSK9-1811 (SEQ ID NO: 14) had the highest activity. This antisense oligonucleotide was completely complementary to the rat and cynomolgus monkey PCSK9 genes, which were used in the efficacy and safety tests described later. For these reasons, this antisense oligonucleotide was selected for subsequent tests.

Test Example 3

HsPCSK9-1811 (SEQ ID NO: 14) having an LNA or AmNA bridging structure was evaluated for efficacy in hyperlipidemic cynomolgus monkeys.

The specific procedure was as follows. Prior to the test, the LDL cholesterol levels of cynomolgus monkeys (purpose-bred, anti-B virus antibody negative, 2 to 4 years old, male) were measured to pre-select animals with high LDL cholesterol levels. From among the pre-selected animals, those with sustained high LDL cholesterol levels at 6 days before administration were selected and used. Each antisense nucleic acid was subcutaneously administered to the selected cynomolgus monkeys on an intermittent schedule at increasing doses, namely, at 1 mg/kg at the start of the test (day 0), at 3 mg/kg on day 7, and at 10 mg/kg on day 14. After that, in the case where significant reduction in blood LDL cholesterol level was observed, the same antisense nucleic acid was additionally administered at decreasing doses, namely, at 3 mg/kg on day 42 and at 1 mg/kg on day 61. The blood LDL cholesterol level was measured with an automated biochemical analyzer (JCA-BM6070, JEOL Ltd.) every 2 or 3 days from the start of the test until day 100. The blood LDL cholesterol level was presented as a relative value compared to that at the start of the test and evaluated. In addition, the blood PCSK9 level after 10 mg/kg administration was measured using CircuLex (registered trademark) Human PCSK9 ELISA Kit (CycLex). The blood PCSK9 level was presented as a relative value compared to that at the time point of 10 mg/kg administration and evaluated. The results are shown in FIG. 3 and FIG. 4.

Figure 3:
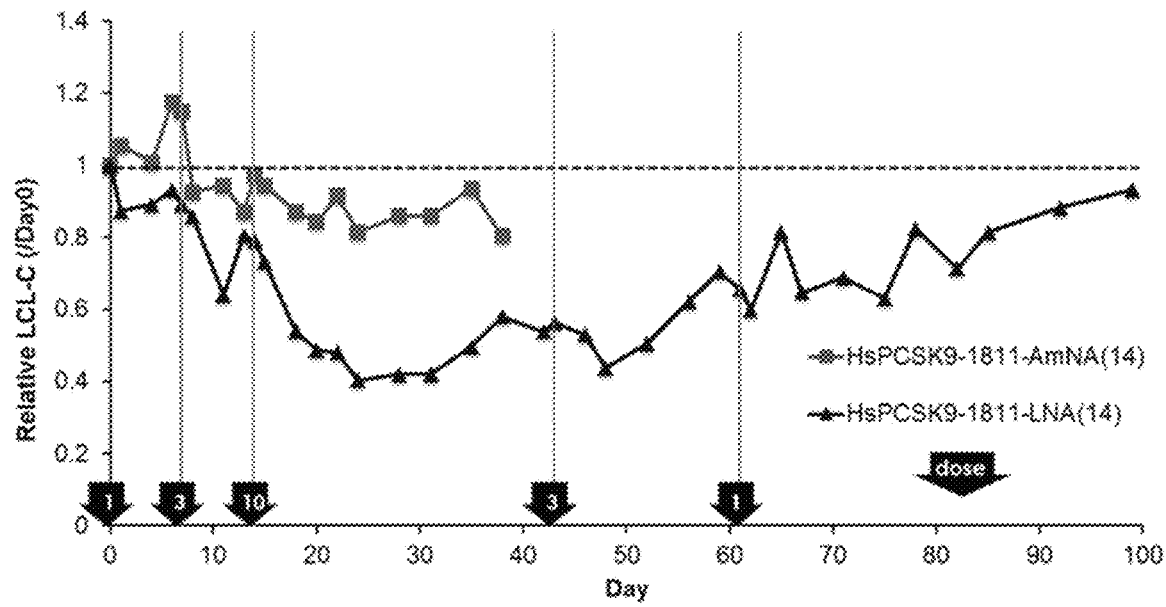
FIG. 3 shows the change in blood LDL cholesterol level in cynomolgus monkeys in conjunction with the dose of the antisense nucleic acid (relative value compared to the level at the start of the test).
Figure 4:
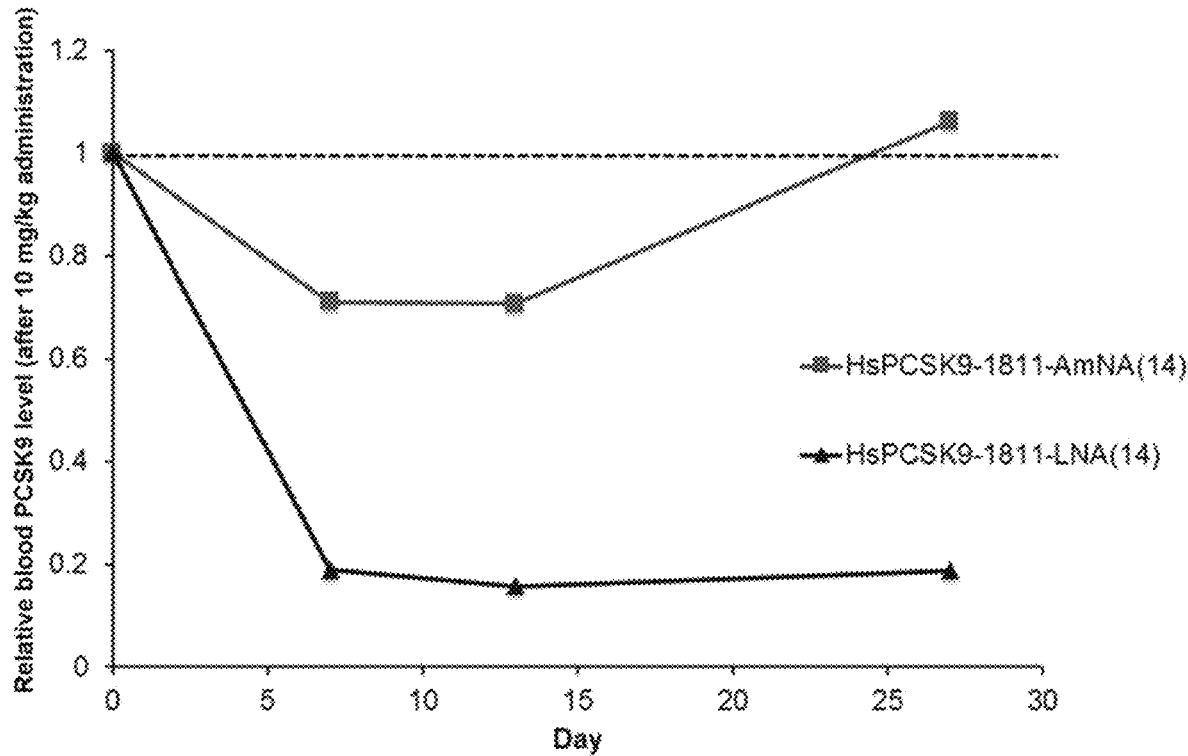
FIG. 4 shows the change in blood PCSK9 level in cynomolgus monkeys after antisense nucleic acid administration at 10 mg/kg (relative value compared to the level at the time point of 10 mg/kg administration).
Figure 5:
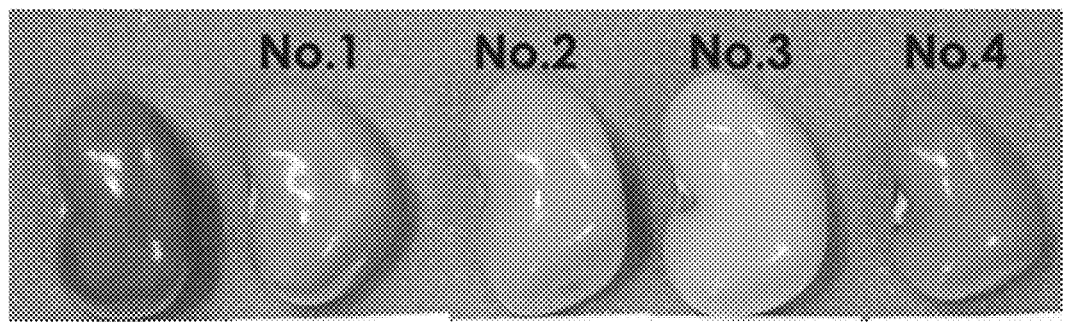
FIG. 5 shows the appearance of the kidneys of cynomolgus monkeys after intermittent administration of an antisense nucleic acid at 10 mg/kg or 30 mg/kg.

As shown in FIG. 3, the blood LDL cholesterol level was reduced after antisense administration regardless of the type of the bridging structure. In the case of the administration of the antisense nucleic acid having an LNA bridging structure, a continuous remarkable reduction (approximately 60% reduction) in blood LDL cholesterol level was observed for 28 days after 10 mg/kg administration. These results were consistent with the results in FIG. 4 showing reduction in blood PCSK9 level, indicating that the antisense nucleic acid exerted its activity. In addition, the blood LDL cholesterol level was reversed by intermittent administration at decreasing doses. The above results demonstrate that the antisense nucleic acid exerted its activity in hyperlipidemic cynomolgus monkeys although the potency varied with the type of the bridging structure.

Test Example 4

HsPCSK9-1811 (SEQ ID NO: 14) having an LNA bridging structure was subjected to a safety test on cynomolgus monkeys.

The specific procedure was as follows. The antisense nucleic acid was subcutaneously administered to cynomolgus monkeys (purpose-bred, anti-B virus antibody negative, 3 to 4 years old, male) at a dose of 10 mg/kg or 30 mg/kg on an intermittent schedule, namely, once a week for 2 weeks (2 times in total) (10 mg/kg administration group: No. 1 and No. 2, 30 mg/kg administration group: No. 3 and No. 4, n=2 per group). After administration, the following observation and analysis were performed: general condition, body weight, feed consumption, water intake, urine analysis, hematological analysis, blood biochemical analysis, necropsy, organ weight, and histopathological analysis. For the urine analysis, an automated biochemical analyzer (JCA-BM6070, JEOL Ltd.) was used, and for the blood biochemical analysis, an automated biochemical analyzer (JCA-BM6070, JEOL Ltd.) was used. The representative results are shown in FIGS. 5 to 8.

Figure 6:
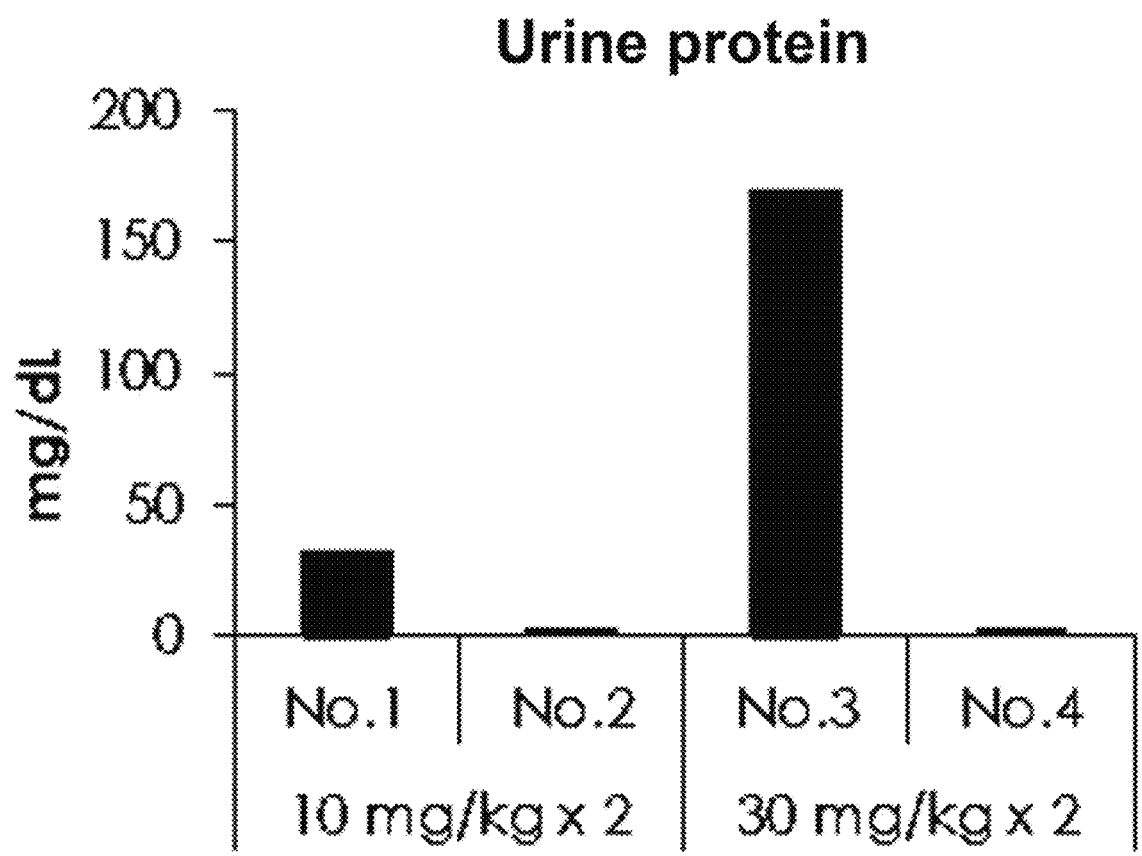
FIG. 6 shows the urine protein level in cynomolgus monkeys after intermittent administration of an antisense nucleic acid at 10 mg/kg or 30 mg/kg.
Figure 7:
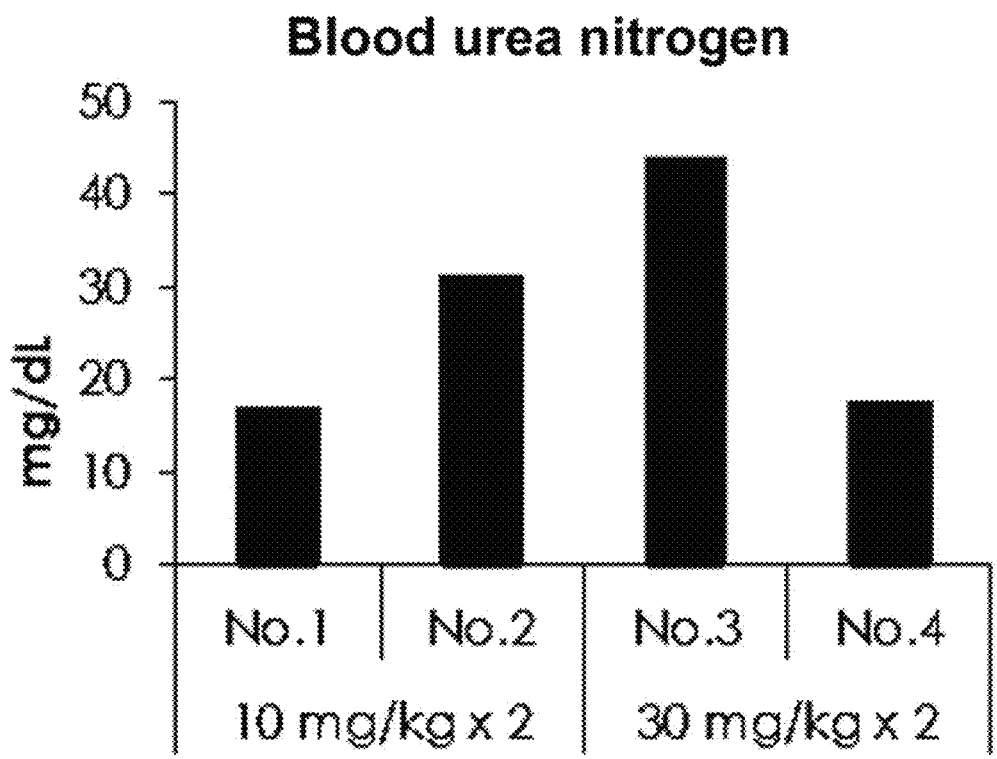
FIG. 7 shows the blood urea nitrogen level in cynomolgus monkeys after intermittent administration of an antisense nucleic acid at 10 mg/kg or 30 mg/kg.
Figure 8:
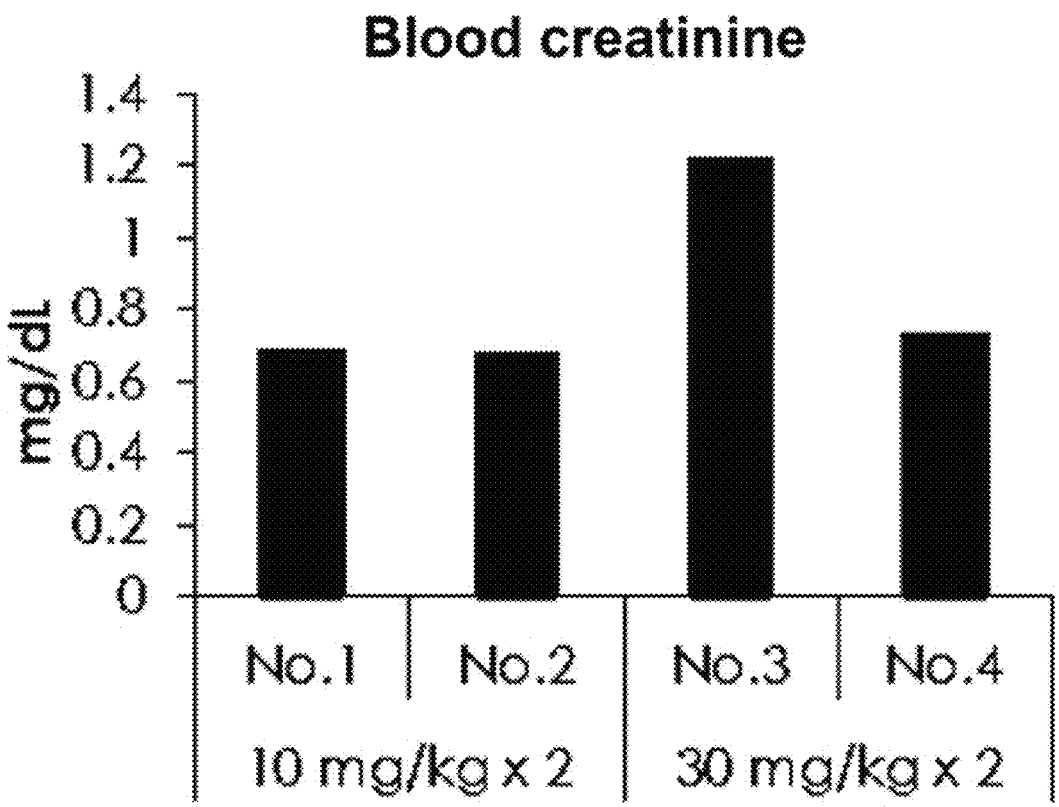
FIG. 8 shows the blood creatinine level in cynomolgus monkeys after intermittent administration of an antisense nucleic acid at 10 mg/kg or 30 mg/kg.

In both the 10 mg/kg and 30 mg/kg administration groups, renal hypertrophy accompanied by kidney weight gain were observed (FIG. 5), and elevated urinary protein levels were also detected by the urine analysis (FIG. 6). In the blood biochemical analysis, elevated blood urea nitrogen levels, which were indicative of renal disorder, were observed in both groups (FIG. 7), and an elevated blood creatinine level was observed in 30 mg/kg administration group (FIG. 8).

The above results indicate that the estimated no-observed-adverse-effect-level (NOAEL) of HsPCSK9-1811-LNA(14) is less than 10 mg/kg. In Test Example 3 as well as the phase I trial of SPC5001 on healthy volunteers, administration of an oligonucleotide alone at an efficacious dose caused adverse effects, in particular, serious renal damage. This finding indicates the need for alteration of oligonucleotides in terms of pharmacokinetics to achieve safer therapy.

Test Example 5

HsPCSK9-1811 (SEQ ID NO: 14) having an LNA bridging structure was subjected to a preliminary toxicity test on rats.

Figure 9:
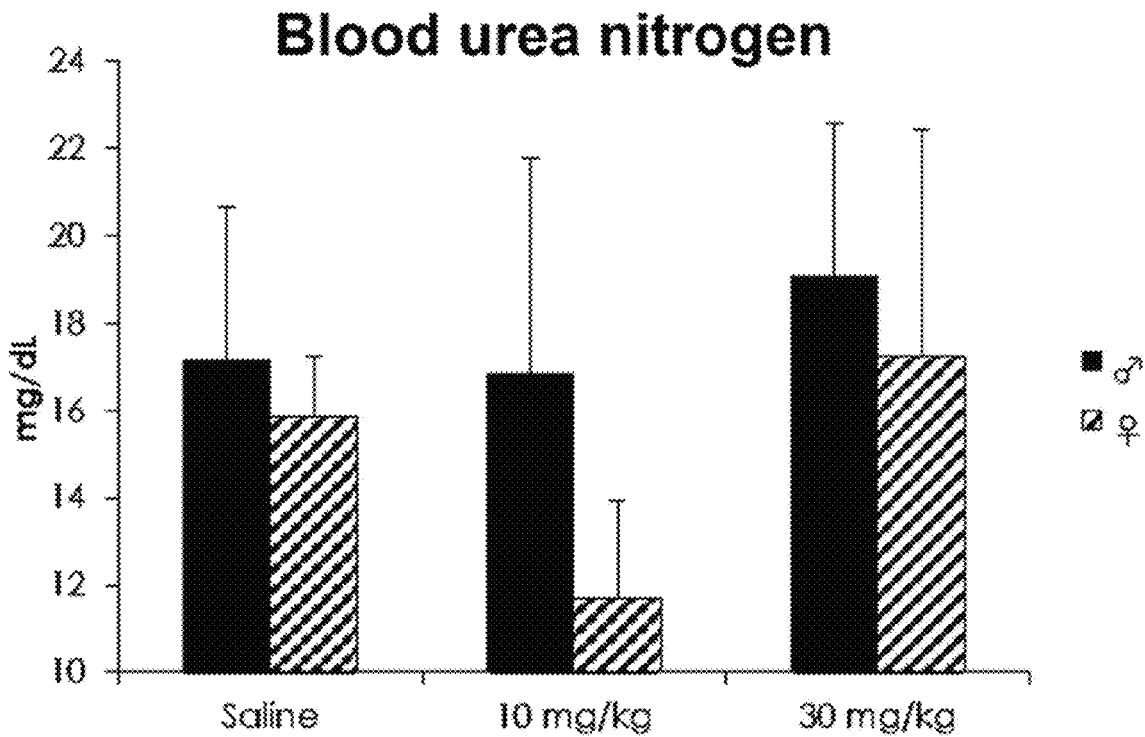
FIG. 9 shows the blood urea nitrogen level in rats after intermittent administration of an antisense nucleic acid at 10 mg/kg or 30 mg/kg.
Figure 10:
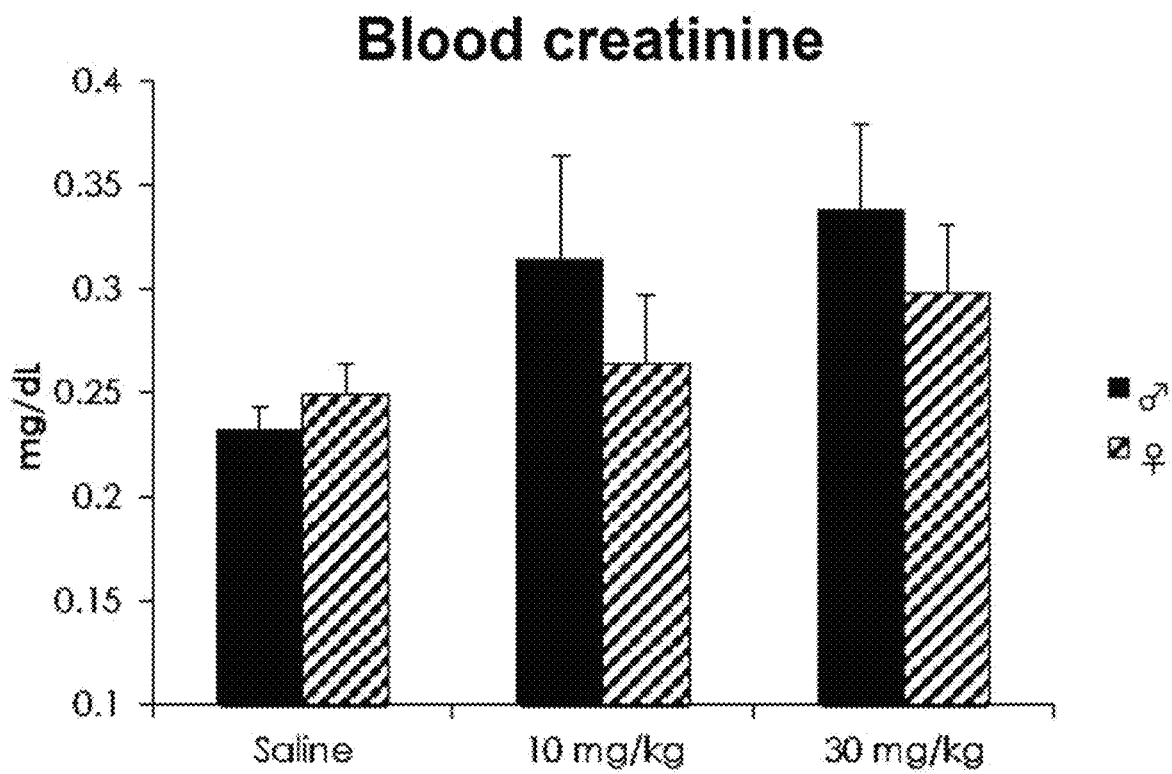
FIG. 10 shows the blood creatinine level in rats after intermittent administration of an antisense nucleic acid at 10 mg/kg or 30 mg/kg.

More specifically, the antisense nucleic acid was subcutaneously administered to rats (Crl:CD (SD), 6 weeks old, Charles River Laboratories Japan, Inc., five males and five females per group) at a dose of 10 mg/kg or 30 mg/kg on an intermittent schedule, namely, once a week for 2 weeks (2 times in total) (n=5). For the control group, physiological saline was subcutaneously administered to rats on the same intermittent schedule as for the antisense-nucleic-acid administration groups. After administration, the following observation and analysis were performed in the same manner as in Test Example 4: general condition, body weight, feed consumption, hematological analysis, blood biochemical analysis, necropsy, organ weight, and histopathological analysis. The representative results are shown in FIG. 9 and FIG. 10.

Similarly to the results of Test Example 4, renal hypertrophy accompanied by kidney weight gain was observed in both the 10 mg/kg and 30 mg/kg administration groups; and elevated blood urea nitrogen levels (FIG. 9) and elevated blood creatinine levels (FIG. 10) were detected by the blood biochemical analysis.

The above results indicate that the estimated no-observed-adverse-effect-level (NOAEL) of HsPCSK9-1811-LNA(14) is less than 10 mg/kg. Similarly to the results of Test Example 4, administration of an oligonucleotide alone at an efficacious dose caused adverse effects, in particular, serious renal damage. This finding indicates the need for alteration of oligonucleotides in terms of pharmacokinetics to achieve safer therapy.

Test Example 6

Figure 11:
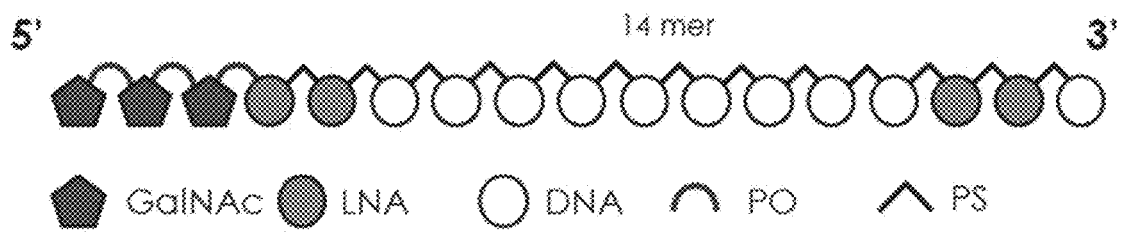
FIG. 11 is a schematic view of the structure of an antisense nucleic acid-GalNAc conjugate.

HsPCSK9-1811 (SEQ ID NO: 14) having an LNA bridging structure, which caused renal damage in Test Example 4 and Test Example 5, was modified by contiguously introducing three GalNAc monomeric units (amidated GalNAc units) by the phosphoramidite method on an automated oligonucleotide synthesizer (OligoPilot 10, GE Healthcare). Thus, an antisense nucleic acid-GalNAc conjugate (HsPCSK9-1811-LNA(14)-GN(3)) was obtained. The schematic view of the 14-mer antisense nucleic acid-GalNAc conjugate is shown in FIG. 11. HsPCSK9-1811-LNA(14)-GN(3) was subjected to an efficacy test on hyperlipidemic cynomolgus monkeys. For the attachment of the GalNAc units, the linkers of the above-described structure (A) were used and illustrated below.

[Chem. 3]

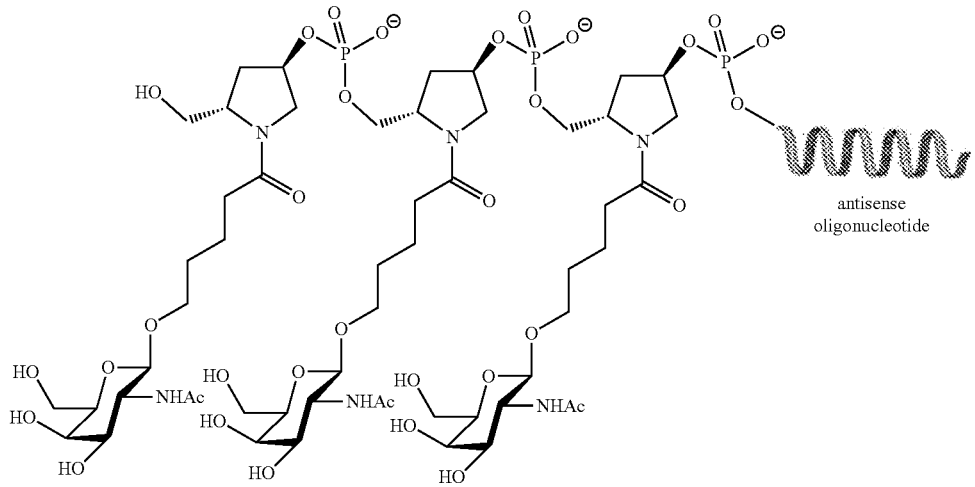

Figure 12:
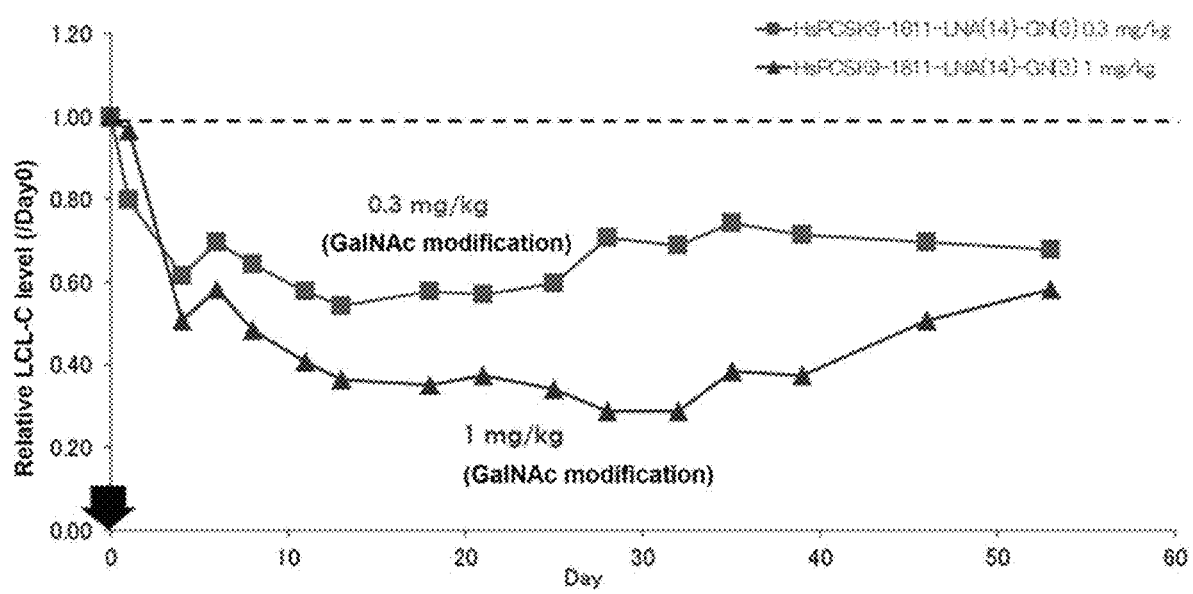
FIG. 12 shows the change in blood LDL cholesterol level in cynomolgus monkeys after single administration of an antisense nucleic acid-GalNAc conjugate at 0.3 mg/kg or 1 mg/kg (relative value compared to the level at the start of the test).
Figure 13:
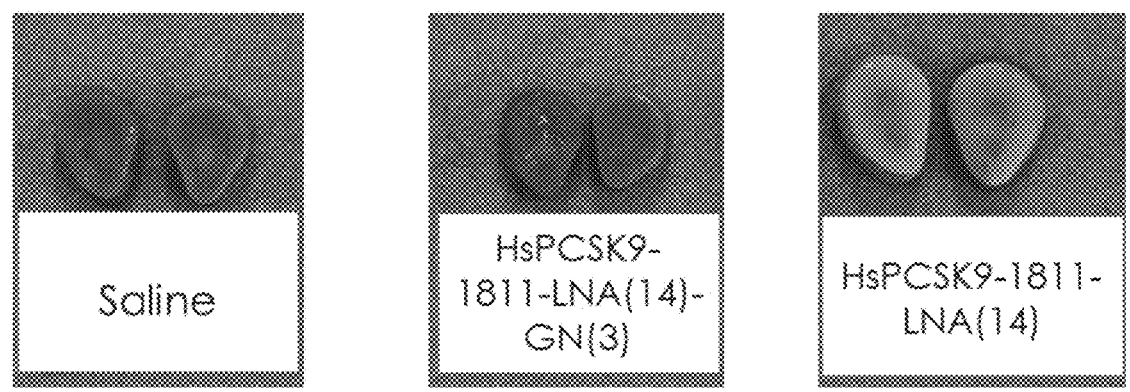
FIG. 13 shows the appearance of the kidneys of rats after intermittent administration of an antisense nucleic acid or an antisense nucleic acid-GalNAc conjugate.
Figure 14:
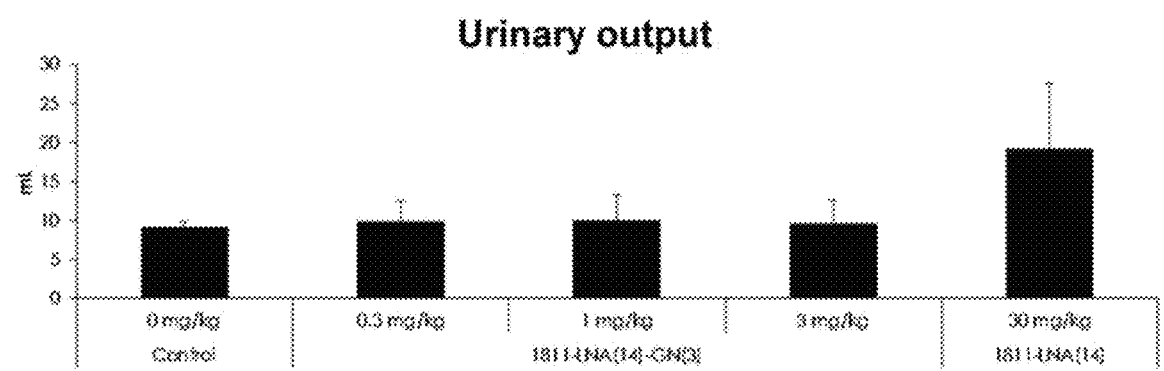
FIG. 14 shows the urinary output in rats after intermittent administration of an antisense nucleic acid or an antisense nucleic acid-GalNAc conjugate.

The specific procedure was as follows. The antisense nucleic acid-GalNAc conjugate was subcutaneously administered to hyperlipidemic cynomolgus monkeys (purpose-bred, anti-B virus antibody negative, 3 to 4 years old, male), which were selected in advance as described in Test Example 3, at a single dose of 0.3 mg/kg or 1 mg/kg (n=1). The blood LDL cholesterol level was measured with an automated biochemical analyzer (JCA-BM6070, JEOL Ltd.) every 2 or 3 days from the start of the test until day 53. The blood LDL cholesterol level was presented as a relative value compared to that at the start of the test and evaluated. The results are shown in FIG. 12.

A remarkable reduction in blood LDL cholesterol level was observed at both doses in hyperlipidemic cynomolgus monkeys. The results indicate that the efficacious dose is about one-thirtieth to one-tenth of that of HsPCSK9-1811-LNA(14).

Test Example 7

HsPCSK9-1811 (SEQ ID NO: 14) having an LNA bridging structure (HsPCSK9-1811-LNA(14)) or HsPCSK9-1811 (SEQ ID NO: 14) having an LNA bridging structure and a GalNAc modification (HsPCSK9-1811-LNA(14)-GN(3)) was subcutaneously administered to male 6-week-old Crl: CD (SD) rats (5 animals per group) on an intermittent schedule for 2 weeks to examine whether there would be difference in toxicity between these oligonucleotides. The efficacious dose of HsPCSK9-1811-LNA(14)-GN(3) was set at 0.3 mg/kg by reference to the results of Test Example 6. The high dose was set at 3 mg/kg, which was 10 times the efficacious dose, and the medium dose was set at 1 mg/kg. The dose of HsPCSK9-1811-LNA(14) was set at 30 mg/kg, at which renal damage had been observed in Test Examples 4 and 5. In each case, the oligonucleotide was administered once a week for 2 weeks (2 times in total). For the control group, physiological saline was subcutaneously administered to rats on the same schedule as for the test substance administration groups. For blood biochemical analysis, an automated biochemical analyzer (JCA-BM6070, JEOL Ltd.) was used. The urinary kidney injury molecule (Kim-1) level was measured with Bio-Plex 200 (Bio-Rad). The representative results are shown in FIGS. 13 to 16.

Figure 15:
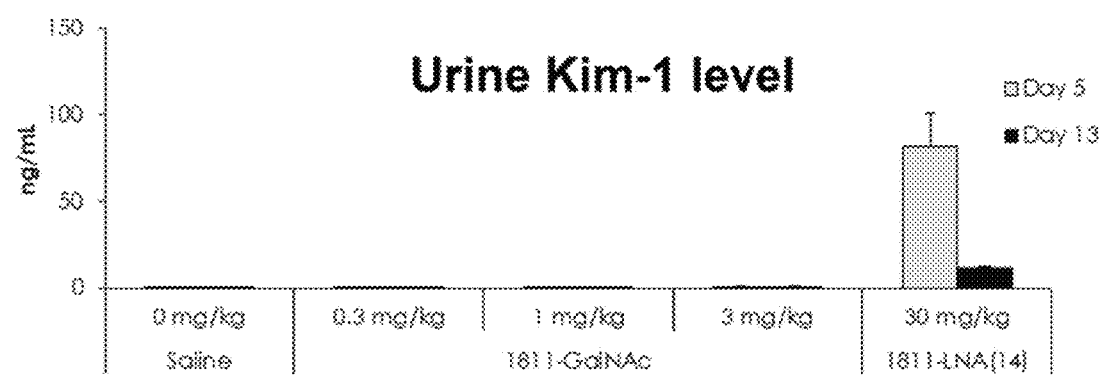
FIG. 15 shows the urine Kim-1 level in rats after intermittent administration of an antisense nucleic acid or an antisense nucleic acid-GalNAc conjugate.
Figure 16:
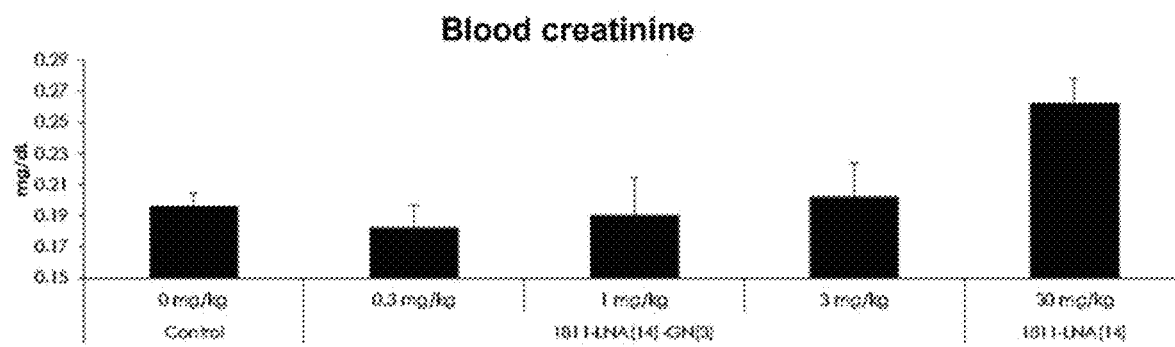
FIG. 16 shows the blood creatinine level in rats after intermittent administration of an antisense nucleic acid or an antisense nucleic acid-GalNAc conjugate.
Figure 17:
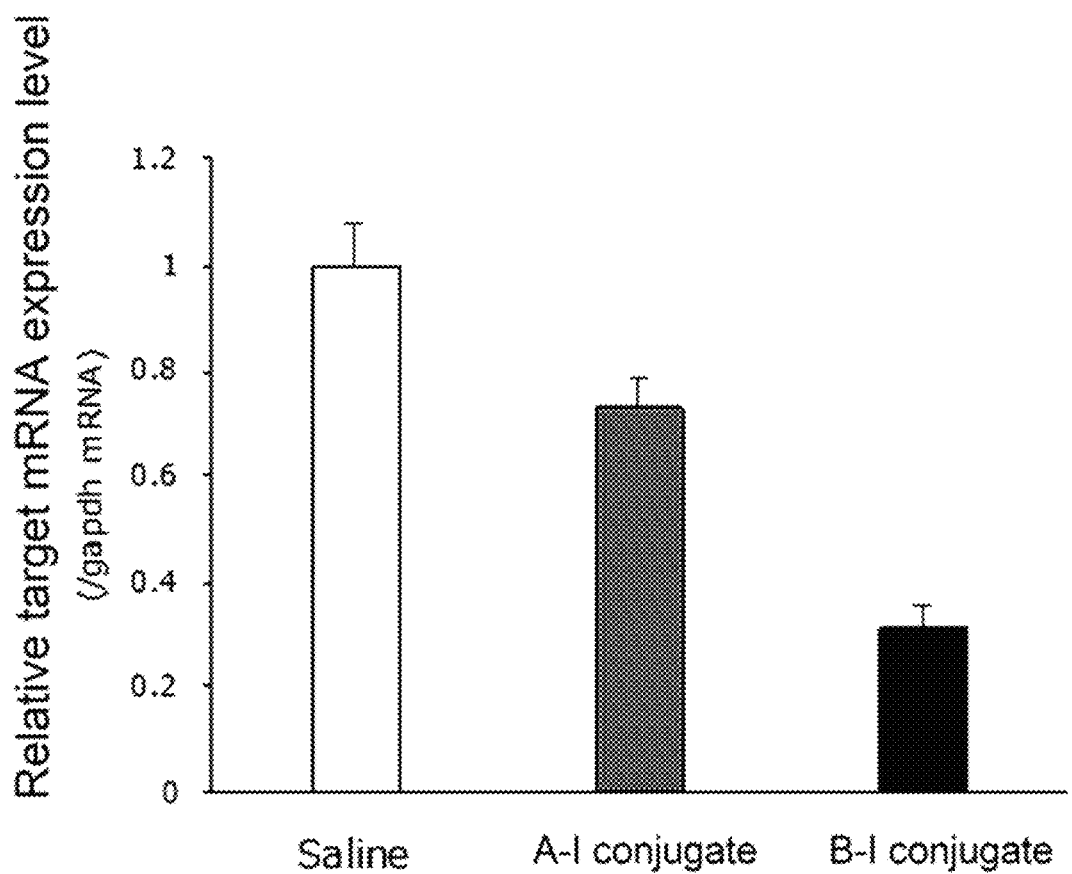
FIG. 17 shows the results of the comparison of the target gene expression levels in mouse livers after single administration of two types of antisense nucleic acid-GalNAc conjugates using different main-chain linker structures for GalNAc connection.

In the HsPCSK9-1811-LNA(14) administration group, renal hypertrophy accompanied by kidney weight gain (FIG. 13) and an elevated blood creatinine level (FIG. 16) were observed and consistent with the results of Test Examples 4 and 5. The urine analysis showed an increase in urinary output (FIG. 14) and an elevated level of urinary kidney injury molecule 1 (Kim-1), an early marker of acute renal damage (FIG. 15). In contrast, the HsPCSK9-1811-LNA(14)-GN(3) administration groups did not show the above change or elevated levels. The histopathological analysis showed that the HsPCSK9-1811-LNA(14) administration group had changes in the kidney, such as degeneration, necrosis, and regeneration in the tubular epithelium, tubular enlargement, hyaline cast formation, and mononuclear cell infiltration into the tubulointerstitium. In contrast, none of the above changes were observed at any dose of HsPCSK9-1811-LNA(14)-GN(3).

Test Example 8

In order to examine whether the activity of an antisense nucleic acid in the liver would be affected by the structure of a main-chain linker used for connection of GalNAc units, an antisense nucleic acid-GalNAc conjugate having linkers of the above-described structure (A) and an antisense nucleic acid-GalNAc conjugate having linkers of the above-described structure (B) were prepared (referred to as conjugate A-I and conjugate B-I, respectively). Saline (physiological saline) or each antisense nucleic acid-GalNAc conjugate was subcutaneously administered to male 8-week-old wild-type mice (Japan SLC, Inc) at a single dose of 17.5 nmol/kg. Three days after administration, livers were excised, and the target gene expression levels were quantified on a real-time PCR system (ABI). The structure for the connection of GalNAc units is illustrated below.

[Chem. 4]

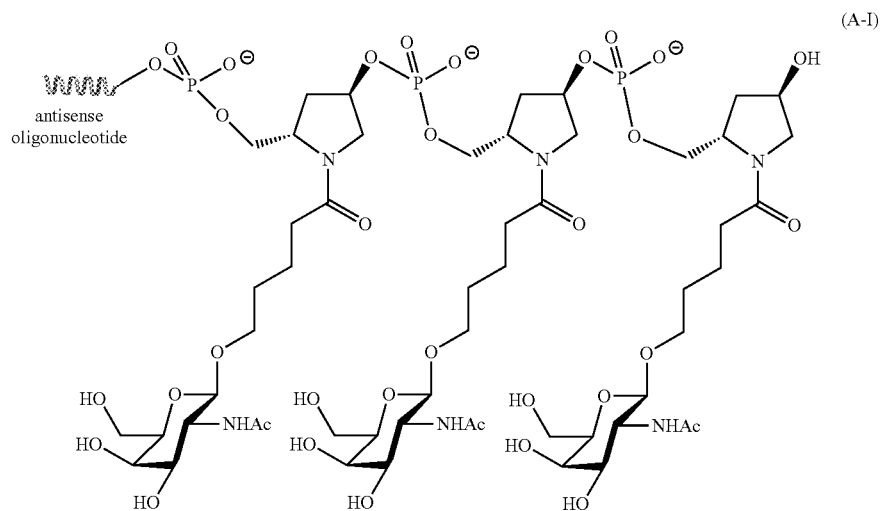

(A-I)

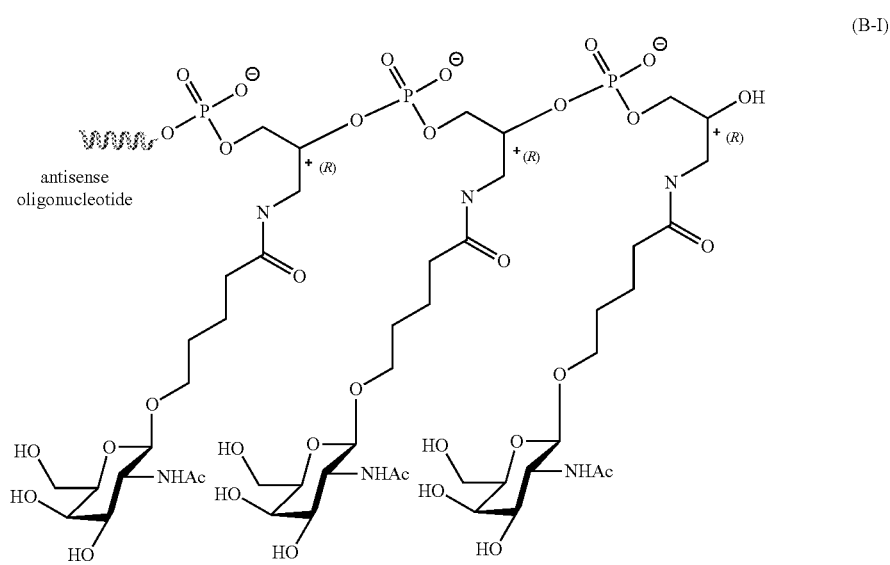

(B-I)

Conjugate B-I with a highly flexible main-chain structure showed higher inhibitory effect on gene expression as compared with conjugate A-I with a less flexible main-chain structure. These results indicate that, in order to maximize the activity of an antisense nucleic acid in hepatocytes, designing a structurally flexible linker, which is more susceptible to intracellular metabolism, is important.

The above results indicate that HsPCSK9-1811-LNA (14)-GN(3) is sufficiently efficacious even when administered at a dose as low as 0.3 to 1 mg/kg once in several weeks and is potentially safer for use in therapy. Also shown is that, for prevention of renal damage, which is a main adverse effect common to antisense oligonucleotide-based drugs, (1) selection of an in vivo highly active antisense oligonucleotide using the CEM method, and (2) production of an antisense oligonucleotide-GalNAc conjugate are effective.

INDUSTRIAL APPLICABILITY

The present invention can be used in the field of pharmaceutical products, in particular, the field of the development and production of therapeutic agents for diseases associated with a high LDL cholesterol level.

The invention claimed is:

1. An oligonucleotide conjugate comprising an oligonucleotide and two or more linearly connected asialoglycoprotein receptor-binding molecules attached to the oligonucleotide, wherein the oligonucleotide comprises a locked nucleoside analog having a bridging structure between the 4' and 2' positions, wherein the oligonucleotide is complementary to a region of a human PCSK9 gene, and the oligonucleotide inhibits expression of the human PCSK9 gene, wherein the oligonucleotide and the asialoglycoprotein receptor-binding molecules is a linkage via a linker, wherein the linker comprises a main-chain linker that binds to the oligonucleotide, and a side-chain linker that is branched from the main-chain and binds to the asialoglycoprotein receptor-binding molecule, and wherein the linker has the following structure (I):

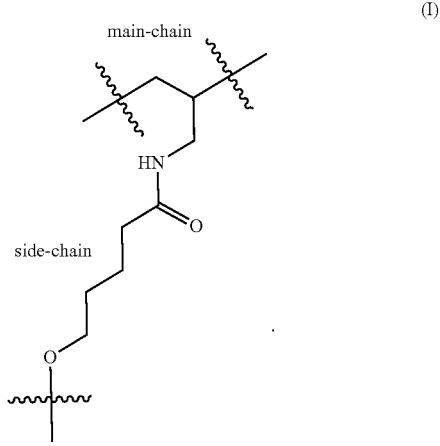 [SMILES: *CC(*)CNC(=O)CCCCO*]

2. The oligonucleotide conjugate according to claim 1, wherein the bridging structure is selected from the following (i) to (iv):
(i) a structure represented by —CH$_2$—O— or —(CH$_2$)$_2$—O—;
(ii) a structure represented by —CH$_2$—NR$^1$—O— or —(CH$_2$)$_2$—NR$^1$—O—;
(iii) a structure represented by —CO—NR$^1$—, —CH$_2$—CO—NR$^1$—, —(CH$_2$)$_2$—CO—NR$^1$—, —CO—NR$^1$—X—, or —CH$_2$—CO—NR$^1$—X—; or
(iv) a structure represented by —CH$_2$—NR$^1$— or —(CH$_2$)$_2$—NR$^1$—
wherein R$^1$ represents a hydrogen atom;
an optionally branched or cyclic alkyl group of 1 to 7 carbon atoms;
an optionally branched or cyclic alkenyl group of 2 to 7 carbon atoms;
an aryl group of 3 to 12 carbon atoms which may have a heteroatom and may have any one or more substituting groups selected from group a consisting of a hydroxyl group, a straight-chain alkyl group of 1 to 6 carbon atoms, a straight-chain alkoxy group of 1 to 6 carbon atoms, a mercapto group, a straight-chain alkylthio group of 1 to 6 carbon atoms, an amino group, a straight-chain alkylamino group of 1 to 6 carbon atoms, and a halogen atom; or
an alkyl group having an aryl moiety of 3 to 12 carbon atoms, which moiety may have a heteroatom or may have any one or more substituting groups selected from the group a, and
X represents an oxygen atom, a sulfur atom, an amino group, or a methylene group.

3. The oligonucleotide conjugate according to claim 1, wherein the oligonucleotide is configured to bind to a region of the human PCSK9 gene represented by a nucleotide sequence comprising any of the following: the nucleotide sequence of SEQ ID NO: 3; the nucleotide sequence of SEQ ID NO: 4; the nucleotide sequence of SEQ ID NO: 5; the nucleotide sequence of SEQ ID NO: 6; the nucleotide sequence of SEQ ID NO: 7; the nucleotide sequence of SEQ ID NO: 8; the nucleotide sequence of SEQ ID NO: 9; the nucleotide sequence of SEQ ID NO: 10; the nucleotide sequence of SEQ ID NO: 11; the nucleotide sequence of SEQ ID NO: 12; the nucleotide sequence of SEQ ID NO: 13; or the nucleotide sequence of SEQ ID NO: 14.

4. The oligonucleotide conjugate according to claim 1, wherein one or more internucleoside linkages are phosphorothioate linkages.

5. The oligonucleotide conjugate according to claim 1, wherein the oligonucleotide conjugate has the linkage between the main-chain linker and the oligonucleotides is phosphodiester bond, or one or more of the linkages between the main-chain linkers are phosphodiester bonds.

6. The oligonucleotide conjugate according to claim 1, wherein the number of the asialoglycoprotein receptor-binding molecules linearly connected is 2 to 5.

7. The oligonucleotide conjugate according to claim 1, wherein the asialoglycoprotein receptor-binding molecules are one or more types of molecules selected from the group consisting of lactose, galactose, N-acetylgalactosamine (GalNAc), galactosamine, N-formylgalactosamine, N-propionylgalactosamine, N-n-butanoylgalactosamine, N-iso-butanoylgalactosamine, and derivatives thereof.

8. The oligonucleotide conjugate according to claim 1, wherein the oligonucleotide has a 10- to 25-base nucleotide sequence.

9. A method for inhibiting a disease associated with a high LDL cholesterol level comprising administering the oligonucleotide conjugate according to claim 1 to a subject in need thereof.

10. The method according to claim 9, wherein the disease associated with a high LDL cholesterol level is hypercholesterolemia.

11. The method according to claim 9, wherein the oligonucleotide conjugate is formulated in an injectable preparation.

12. A linker, which joins an oligonucleotide to an asialoglycoprotein receptor-binding molecule, the linker comprising:
a main-chain linker that binds to the oligonucleotide, and
a side-chain linker that is branched from the main-chain and binds to the asialoglycoprotein receptor-binding molecule,
wherein the linker has the following structure (I):

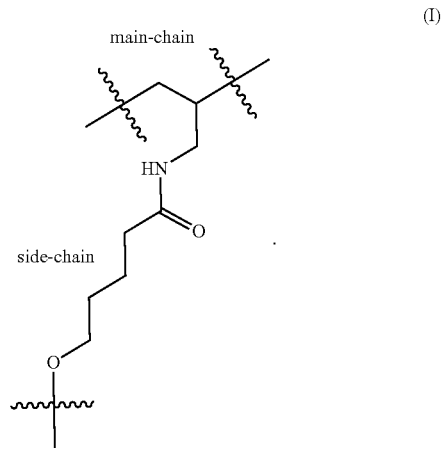 [SMILES: *CC(*)CNC(=O)CCCCO*]

(I)

* * * * *